(12) United States Patent
Mizushima et al.

(10) Patent No.: US 8,921,302 B2
(45) Date of Patent: Dec. 30, 2014

(54) AQUEOUS HAIR CLEANING AGENT

(75) Inventors: Hiroki Mizushima, Wakayama (JP);
Azusa Kasuga, Sumida-ku (JP); Eiji Terada, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/114,826

(22) PCT Filed: May 1, 2012

(86) PCT No.: PCT/JP2012/061572
§ 371 (c)(1),
(2), (4) Date: Oct. 30, 2013

(87) PCT Pub. No.: WO2012/150714
PCT Pub. Date: Nov. 8, 2012

(65) Prior Publication Data
US 2014/0087989 A1    Mar. 27, 2014

(30) Foreign Application Priority Data
May 2, 2011   (JP) .................................. 2011-102880

(51) Int. Cl.
| | | |
|---|---|---|
| C11D 1/02 | (2006.01) | |
| A61Q 5/02 | (2006.01) | |
| A61K 8/41 | (2006.01) | |
| A61K 8/86 | (2006.01) | |
| A61K 8/365 | (2006.01) | |
| A61K 8/73 | (2006.01) | |

(52) U.S. Cl.
CPC ......... *A61K 8/416* (2013.01); *A61K 2800/5426* (2013.01); *A61K 8/86* (2013.01); *A61Q 5/02* (2013.01); *A61K 8/365* (2013.01); *A61K 8/731* (2013.01)
USPC ........... 510/473; 510/119; 510/121; 510/127; 510/421; 510/426; 510/488; 510/492; 510/504; 424/494; 424/70.13; 424/70.22

(58) Field of Classification Search
USPC ......... 510/119, 121, 127, 421, 426, 473, 488, 510/492, 504; 424/494, 70.13, 70.22
See application file for complete search history.

(56) References Cited

U.S. PATENT DOCUMENTS

| | | | |
|---|---|---|---|
| 3,472,840 A | 10/1969 | Stone et al. | |
| 3,816,616 A | 6/1974 | Anguillo et al. | |
| 2011/0213139 A1 * | 9/2011 | Chan et al. | ................. 536/123.1 |
| 2012/0015894 A1 | 1/2012 | Terada | |
| 2012/0214985 A1 | 8/2012 | Takai et al. | |
| 2012/0230934 A1 | 9/2012 | Doi et al. | |
| 2014/0094423 A1 | 4/2014 | Terada | |

FOREIGN PATENT DOCUMENTS

| | | |
|---|---|---|
| EP | 1 676 566 A1 | 7/2006 |
| EP | 1 862 160 A1 | 12/2007 |
| JP | 45-20318 | 7/1970 |
| JP | 59 42681 | 10/1984 |
| JP | 5 148123 | 6/1993 |
| JP | 2005 60270 | 3/2005 |
| JP | 2008 37849 | 2/2008 |
| JP | 2011 94033 | 5/2011 |
| JP | 2012 232934 | 11/2012 |
| JP | 2012 232945 | 11/2012 |
| JP | 2012 232946 | 11/2012 |
| JP | 2012 246286 | 12/2012 |
| WO | 2010/113446 A1 | 10/2010 |
| WO | 2011 059063 | 5/2011 |
| WO | WO 2011/052733 A1 | 5/2011 |
| WO | 2012 091072 | 7/2012 |

OTHER PUBLICATIONS

International Preliminary Report on Patentability and Written Opinion issued Nov. 14, 2013 in PCT/JP2012/061572 (English translation only).
International Search Report Issued Aug. 14, 2012 in PCT/JP12/061572 Filed May 1, 2012.
Extended European Search Report dated Nov. 6, 2014 issued in corresponding EP patent application No. 12779895.7.

* cited by examiner

*Primary Examiner* — Brian P Mruk
(74) *Attorney, Agent, or Firm* — Oblon, Spivak, McClelland, Maier & Neustadt, L.L.P.

(57) ABSTRACT

Provided is an aqueous hair cleansing composition, including the following components (A) to (D) and water, in which the aqueous hair cleansing composition has a pH of from 2 to 5 when diluted 20-fold: (A) an anionic surfactant; (B) a cationized hydroxypropyl cellulose having a main chain derived from an anhydroglucose, and having a degree of substitution with cationized ethyleneoxy groups of from 0.01 to 2.9 and a degree of substitution with propyleneoxy groups of from 0.1 to 4.0; (C) an organic solvent selected from (C1) and (C2): (C1) an aromatic alcohol; and (C2) a polypropylene glycol having a molecular weight of from 200 to 1,000; and (D) a hydroxy monocarboxylic acid or a dicarboxylic acid.

14 Claims, No Drawings

AQUEOUS HAIR CLEANING AGENT

CROSS REFERENCE TO RELATED APPLICATION

This application is a 371 of PCT/JP2012/061572, filed on May 1, 2012, and claims priority to Japanese Patent Application No.2011-102880, filed on May 2, 2011.

FIELD OF THE INVENTION

The present invention relates to an aqueous hair cleansing composition.

BACKGROUND OF THE INVENTION

In recent years where hair damage has been steadily observed owing to the widespread use of a coloring agent or a perm agent, it has become important for a hair cleansing composition to have a function of imparting a conditioning effect in addition to basic functions as a cleansing composition such as foaming and cleaning power.

In general, the following attempts have been made to impart smoothness to hairs. An anionic surfactant and silicones are used in combination (Patent Document 1), or the anionic surfactant and a cationized cellulose are used in combination.

CITATION LIST

Patent Document

[Patent Document 1] JP-A-05-148123

SUMMARY OF THE INVENTION

The present invention provides an aqueous hair cleansing composition, including the following components (A), (B), (C), and (D), and water, in which the aqueous hair cleansing composition has a pH from 2 to 5 at 25° C. when diluted 20-fold by mass with water:

(A) an anionic surfactant;

(B) a cationized hydroxypropyl cellulose having a main chain derived from an anhydroglucose represented by the following general formula (1), and having a degree of substitution with cationized ethyleneoxy groups of from 0.01 to 2.9 and a degree of substitution with propyleneoxy groups of from 0.1 to 4.0:

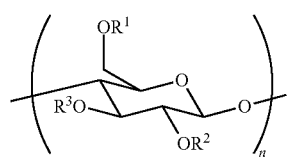
(1)

wherein, in the general formula (1), $R^1$, $R^2$, and $R^3$ each independently represent a substituent represented by the following general formula (2), and n represents an average degree of polymerization of the anhydroglucose and is from 50 to 5,000;

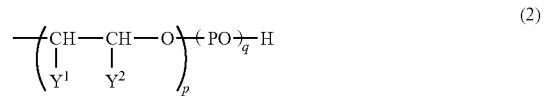
(2)

wherein, in the general formula (2), one of $Y^1$ and $Y^2$ represents a hydrogen atom and the other represents a cationic group represented by the following general formula (3), PO represents a propyleneoxy group, p represents the number of cationized ethyleneoxy groups ($-CH(Y^1)-CH(Y^2)-O-$), q represents the number of propyleneoxy groups ($-PO-$), and p and q each represent 0 or a positive integer, provided that a case where all p's and q's in $R^1$, $R^2$, and $R^3$ simultaneously represent 0 is excluded, and when both p and q do not represent 0, the cationized ethyleneoxy group and the propyleneoxy group may be added in any order, and when both p and q do not represent 0, and p and/or q each represent/represents 2 or more, any one of a block bond and a random bond is permitted;

(3)

wherein, in the general formula (3), $R^4$, $R^5$, and $R^6$ each independently represent a linear or branched alkyl group having from 1 to 3 carbon atoms, and $X^-$ represents an anionic group; (C) one or two or more organic solvents selected from the group consisting of the following components (C1) and (C2):

(C1) an aromatic alcohol represented by the following general formula (4):

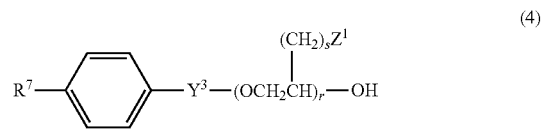
(4)

wherein, in the general formula (4), $R^7$ represents a hydrogen atom, a methyl group, or a methoxy group, $Y^3$ represents a single bond, or a linear or branched alkylene group or alkenylene group having from 1 to 3 carbon atoms, $Z^1$ represents a hydrogen atom or a hydroxyl group, and r and s each represent a number of from 0 to 5; and (C2) a polypropylene glycol having a molecular weight of from 200 to 1,000; and (D) one or two or more organic carboxylic acids selected from the group consisting of a hydroxy monocarboxylic acid and a dicarboxylic acid.

DETAILED DESCRIPTION OF THE INVENTION

In the prior art, smoothness can be imparted to hairs. However, the prior art had room for improvement in the suppression of the entanglement of hair and the volume of hair after drying. In particular, when hairs damaged by a chemical treatment or a heat treatment are entangled after drying, the entanglement may be a cause for additional damage to the hairs upon brushing or the like.

The present invention relates to an aqueous hair cleansing composition that effectively suppresses the entanglement of hair, and the volume of hair, after drying even when hair is damaged hair, and that can impart bounce and resilience to hair.

An aqueous hair cleansing composition of the present invention contains the following components (A) to (D) and water:
(A) an anionic surfactant;
(B) a cationized hydroxypropyl cellulose;
(C) one or two or more organic solvents selected from the group consisting of the components (C1) and (C2); and
(D) one or two or more organic carboxylic acids selected from the group consisting of a hydroxy monocarboxylic acid and a dicarboxylic acid.

Hereinafter, each of the components (A) to (D) is described by taking a specific example. It should be noted that one kind of the respective components can be used alone, or two or more kinds thereof can be used in combination.

(Component (A): Anionic Surfactant)

Specific examples of the anionic surfactant as the component (A) include: sulfate-type anionic surfactants such as an alkyl sulfate, an alkenyl sulfate, a polyoxyalkylene alkyl ether sulfate, a polyoxyalkylene alkenyl ether sulfate, and a sulfosuccinic acid alkylene alkyl phenyl ether sulfate; sulfonic acid-type anionic surfactants such as a sulfosuccinic acid alkyl ester salt, a polyoxyalkylene sulfosuccinic acid alkyl ester salt, and an alkane sulfonate; and carboxylic acid-type anionic surfactants such as a higher fatty acid salt and an alkyl ether carboxylic acid or a salt thereof. Of those, a polyoxyalkylene alkyl ether sulfate, a polyoxyalkylene alkenyl ether sulfate, an alkyl sulfate, and an alkenyl sulfate are preferred, and a polyoxyethylene alkyl ether sulfate represented by the following general formula (11) is more preferred.

$$R^{11}O(CH_2CH_2O)_uSO_3M \quad (11)$$

In the general formula (11), $R^{11}$ represents an alkyl group or alkenyl group having from 10 to 18 carbon atoms, M represents an alkali metal, an alkaline earth metal, ammonium, an alkanolamine, or a basic amino acid, and u represents the average number of added moles of ethylene oxide and represents a number of from 0.5 to 5 in terms of a mass average.

Of those, such a polyoxyethylene alkyl ether sulfate that $R^{11}$ in the general formula (11) represents an alkyl group having from 12 to 14 carbon atoms is more preferred from the viewpoint of achieving compatibility between quick foaming and good feeling of foam. In addition, the average number of added moles of ethylene oxide is preferably from 0.9 to 4, more preferably from 1 to 3. Further, such a polyoxyethylene alkyl ether sulfate that M represents ammonium or sodium is preferred.

The content of the component (A) is preferably 3% by mass or more, more preferably 5% by mass or more, even more preferably 7% by mass or more with respect to the entirety of the aqueous hair cleansing composition from the viewpoint of additionally improving foaming. In addition, the content of the component (A) with respect to the entirety of the aqueous hair cleansing composition is preferably 20% by mass or less, more preferably 18% by mass or less, even more preferably 15% by mass or less from the viewpoints of improving rinse-off characteristics and suppressing a residual feeling in rinsing.

(Component (B): Cationized Hydroxypropyl Cellulose)

The cationized hydroxypropyl cellulose (hereinafter sometimes referred to as "C-HPC") as the component (B) has a main chain derived from an anhydroglucose represented by the following general formula (1).

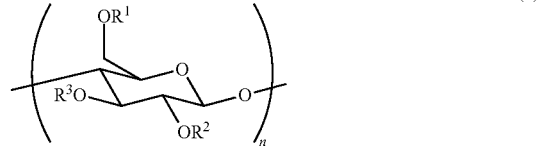

In the general formula (1), $R^1$, $R^2$, and $R^3$ each independently represent a substituent represented by the general formula (2) to be described later, and $R^1$, $R^2$, and $R^3$ may be identical to or different from each other. In addition, n $R^1$'s, n $R^2$'s, and n $R^3$'s may each be identical to or different from each other.

In addition, in the general formula (1), the average degree of polymerization n of the anhydroglucose is 50 or more, preferably 100 or more, more preferably 200 or more, even more preferably 300 or more from the viewpoint of imparting bounce and resilience to hair. In addition, the average degree of polymerization n is 5,000 or less, preferably 3,000 or less, more preferably 2,000 or less, even more preferably 1,500 or less from the viewpoints of: suppressing a residual feeling in rinsing; suppressing the entanglement of hair, and the volume of hair after drying; and improving the ease of production of the compound represented by the general formula (1). With all of those viewpoints considered, the average degree of polymerization n in the general formula (1) is from 50 to 5,000, preferably from 100 to 3,000, more preferably from 200 to 2,000, even more preferably from 300 to 1,500.

It should be noted that the average degree of polymerization in the general formula (1) as used herein refers to a viscosity average degree of polymerization measured by a copper-ammonia method and is specifically calculated by a method described in Examples to be described later.

Next, the general formula (2) is described.

$R^1$, $R^2$, and $R^3$ in the general formula (1) each have a cationized ethyleneoxy group and a propyleneoxy group as represented by the following general formula (2).

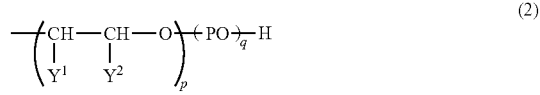

In the general formula (2), one of $Y^1$ and $Y^2$ represents a hydrogen atom and the other represents a cationic group represented by the general formula (3) to be described later. When a plurality of substituents represented by the general formula (2) are present in the general formula (1), the substituents may be different from each other in $Y^1$ or $Y^2$. PO represents a propyleneoxy group.

In the general formula (2), p represents the number of cationized ethyleneoxy groups ($-CH(Y^1)-CH(Y^2)-O-$) in the general formula (2) and represents 0 or a positive integer. p preferably represents 0 or 1 from the viewpoint of additionally improving the ease of production.

In addition, in the general formula (2), q represents the number of propyleneoxy groups ($-PO-$) in the general formula (2) and represents 0 or a positive integer. q represents preferably an integer of 0 to 4, more preferably an integer of 0 to 2, even more preferably 0 or 1 from the viewpoint of additionally improving the ease of production.

It should be noted that the case where p's and q's in all of $R^1$, $R^2$, and $R^3$ in the general formula (2) each represent 0 is excluded. That is, at least one of n $R^1$'s, n $R^2$'s, and n $R^3$'s is such that p in the general formula (2) does not represent 0, and at least one of the substituents is such that q in the general formula (2) does not represent 0.

In addition, when a plurality of substituents represented by the general formula (2) are present in the general formula (1), the substituents may be different from each other in value for p or q.

The total of p and q in one substituent is preferably an integer of 1 to 5, more preferably an integer of 1 to 4, even more preferably an integer of 1 to 3, even more preferably 1 or 2 from the viewpoint of the ease of production. More specifically, with regard to each of $R^1$, $R^2$, and $R^3$ in the general formula (1), p and q in the general formula (2) each preferably represent 0 or 1.

It should be noted that when none of p and q represents 0, the order in which the cationized ethyleneoxy group and the propyleneoxy group are added does not matter. However, the order represented in the general formula (2) is preferred from the viewpoint of the ease of production.

In addition, when none of p and q represents 0, and p and/or q each represent/represents 2 or more, any one of a block bond and a random bond is permitted. However, a block bond is preferred from the viewpoint of the ease of production.

Next, the general formula (3) is described.

One of $Y^1$ or $Y^2$ in the general formula (2) represents a cationic group represented by the following general formula (3).

In the general formula (3), $R^4$, $R^5$, and $R^6$ each independently represent a linear or branched alkyl group having from 1 to 3 carbon atoms, and specific examples thereof include a methyl group, an ethyl group, an n-propyl group, and an isopropyl group. Of those, with regard to each of $Y^1$ and $Y^2$ in the general formula (2), $R^4$, $R^5$, and $R^6$ in the general formula (3) each independently represent preferably a methyl group or an ethyl group, more preferably a methyl group from the viewpoint of improving the water solubility of the C-HPC.

In addition, in the general formula (3), $X^-$ represents an anionic group as a counter ion to an ammonium group.

$X^-$ is not particularly limited as long as it represents an anionic group. Specific examples thereof include an alkyl sulfate ion, a sulfate ion, a phosphate ion, an alkyl carbonate ion, and a halide ion. Of those, a halide ion is preferred from the viewpoint of the ease of production.

Examples of the halide ion include a fluoride ion, a chloride ion, a bromide ion, and an iodide ion. Of those, a chloride ion and a bromide ion are preferred, and a chloride ion is more preferred from the viewpoints of the water solubility and chemical stability of the C-HPC.

Next, the degree of substitution of the component (B) is described.

In the component (B), a degree of substitution with cationized ethyleneoxy groups is from 0.01 to 2.9 and a degree of substitution with propyleneoxy groups is from 0.1 to 4.0.

In the present invention, the degree of substitution with cationized ethyleneoxy groups refers to the average number of moles of cationized ethyleneoxy groups present in the molecule of the C-HPC per 1 mole of the anhydroglucose unit constituting the cellulose main chain.

In the C-HPC represented by the general formula (1), the degree of substitution with cationized ethyleneoxy groups is 2.9 or less, preferably 2.0 or less, more preferably 1.0 or less, even more preferably 0.5 or less from the following viewpoints. At the time of hair washing with the aqueous hair cleansing composition of the present invention, the composition foams well, is excellent in rinse-off characteristics, effectively suppresses the entanglement of hair, and the volume of hair, after drying even when hair is damaged hair, and imparts bounce and resilience to hair. In addition, the degree is 0.01 or more, preferably 0.02 or more from the following viewpoints. At the time of hair washing with the aqueous hair cleansing composition of the present invention, the composition foams well, is excellent in rinse-off characteristics, effectively suppresses the entanglement of hair, and the volume of hair, after drying even when hair is damaged hair, and imparts bounce and resilience to hair. With all of those viewpoints considered, the degree of substitution with cationized ethyleneoxy groups is from 0.01 to 2.9, preferably from 0.01 to 2.0, more preferably from 0.02 to 1.0, even more preferably from 0.02 to 0.5.

In addition, in the present invention, the degree of substitution with propyleneoxy groups refers to the average number of moles of propyleneoxy groups present in the molecule of the C-HPC per 1 mole of the anhydroglucose unit constituting the cellulose main chain.

The degree of substitution with propyleneoxy groups is 4.0 or less, preferably 3.0 or less, more preferably 2.5 or less, even more preferably 2.1 or less from the viewpoint of the ease of production and the following viewpoints. At the time of hair washing with the aqueous hair cleansing composition of the present invention, the composition foams well, is excellent in rinse-off characteristics, effectively suppresses the entanglement of hair, and the volume of hair, after drying even when hair is damaged hair, and imparts bounce and resilience to hair. In addition, the degree is 0.1 or more, preferably 0.2 or more, more preferably 0.5 or more, even more preferably 0.8 or more from the following viewpoints. At the time of hair washing with the aqueous hair cleansing composition of the present invention, the composition foams well, is excellent in rinse-off characteristics, effectively suppresses the entanglement of hair, and the volume of hair, after drying even when hair is damaged hair, and imparts bounce and resilience to hair. With all of those viewpoints considered, the degree of substitution with propyleneoxy groups is from 0.1 to 4.0, preferably from 0.2 to 3.0, more preferably from 0.5 to 2.5, even more preferably from 0.8 to 2.1.

Further, in the general formula (2), the sum of the degree of substitution with cationized ethyleneoxy groups and the degree of substitution with propyleneoxy groups is preferably 3.2 or less, more preferably 3.0 or less, even more preferably 2.5 or less. In addition, the sum is preferably 0.11 or more, more preferably 0.2 or more, even more preferably 0.3 or more from the following viewpoints. At the time of hair washing with the aqueous hair cleansing composition, the composition foams well, is excellent in rinse-off characteristics, effectively suppresses the entanglement of hair, and the volume of hair, after drying even when hair is damaged hair, and imparts bounce and resilience to hair. With all of those viewpoints considered, the sum of the degree of substitution with cationized ethyleneoxy groups and the degree of substitution with propyleneoxy groups is preferably from 0.11 to 3.2, more preferably from 0.2 to 3.0, even more preferably from 0.3 to 2.5.

In addition, a combination of the constructions of $R^1$, $R^2$, and $R^3$ in the general formula (1) is, for example, such a construction that: with regard to $R^1$, in the general formula (2), p represents 1, q represents 0, and one of $Y^1$ and $Y^2$ represents a hydrogen atom and the other represents a cationic group represented by the general formula (3), and in the general formula (3), each of $R^4$, $R^5$, and $R^6$ represents a methyl group, and $X^-$ represents a chloride ion; and with regard to each of $R^2$ and $R^3$, in the general formula (2), p represents 0 and q represents 0 or 1.

The content of the C-HPC as the component (B) is preferably 0.01% by mass or more, more preferably 0.02% by mass or more, even more preferably 0.05% by mass or more, even more preferably 0.1% by mass or more with respect to the entirety of the aqueous hair cleansing composition from the viewpoints of: improving the stability of foam to obtain rich foaming; and obtaining a suppressing effect on the entanglement of hair after drying at the time of rinsing with additional reliability. In addition, the content is preferably 10% by mass or less, more preferably 5% by mass or less, even more preferably 2% by mass or less, even more preferably 1% by mass or less with respect to the entirety of the aqueous hair cleansing composition from the viewpoints of improving rinse-off characteristics and suppressing a residual feeling in rinsing. With all of those viewpoints considered, the content of the C-HPC is preferably from 0.01 to 10% by mass, more preferably from 0.02 to 5% by mass, even more preferably from 0.05 to 2% by mass, even more preferably from 0.1 to 1% by mass.

In addition, the mass ratio (component (B)/component (A)) of the component (B) to the component (A) in the aqueous hair cleansing composition of the present invention is preferably 0.0005 or more, more preferably 0.001 or more, even more preferably 0.006 or more from the viewpoints of: improving the stability of foam to obtain rich foaming; imparting bounce and resilience to hair; and effectively suppressing the entanglement of hair and the volume of hair, after drying. In addition, the ratio "component (B)/component (A)" in the aqueous hair cleansing composition of the present invention is preferably 0.5 or less, more preferably 0.1 or less, even more preferably 0.05 or less from the viewpoints of: improving rinse-off characteristics; suppressing a residual feeling in rinsing; and effectively suppressing the entanglement of hair, and the volume of hair after drying.

Next, a method of producing the cationized hydroxypropyl cellulose as the component (B) is described.

The C-HPC can be obtained by, for example, any one of the following production methods (1) to (3):
(1) a method involving mixing a cellulose, a large amount of water, and a large excess of an alkali metal hydroxide in a slurry state, and causing the mixture to react with a cationizing agent and propylene oxide;
(2) a method involving using dimesyl acetamide containing lithium chloride as a solvent, further adding amines and an alcoholate catalyst to dissolve a cellulose, and causing the solution to react with a cationizing agent and propylene oxide; or
(3) a method involving causing a powdery, pellet-shaped, or chip-shaped cellulose, a cationizing agent, and propylene oxide to react with one another in the coexistence of a base without using excess water or a solvent unlike the method (1) or (2).

In each of the production methods (1) to (3), which one of a reaction with the cationizing agent and a reaction with propylene oxide is performed earlier is not limited, and the reactions may be simultaneously performed.

Of those production methods, the production method (3) is preferred from the viewpoint of the ease of production.

The production method (3) preferably includes the following first and second steps. In addition, in the present invention, the cationizedhydroxypropyl cellulose as the component (B) is preferably a cationized hydroxypropyl cellulose obtained by a production method including the following first step and second step.

First step: a step involving adding the cationizing agent to pulp, performing a crystallinity reduction through a pulverizer treatment, adding a base to the resultant, and performing a reaction between the pulp and the cationizing agent, while performing a crystallinity reduction through a pulverizer treatment, to provide a cationized cellulose Second step: a step involving causing the cationized cellulose obtained in the first step and propylene oxide to react with each other to provide the cationized hydroxypropyl cellulose A cationized hydroxypropyl cellulose showing a small molecular weight reduction and having high water solubility can be efficiently produced by the production method with additionally high productivity.

Hereinafter, the production method (3) is specifically described.

(Raw Material Cellulose)

The reactivity of the crystalline moiety of a cellulose for producing the C-HPC is generally low. Accordingly, (i) a low-crystalline and powdery cellulose whose crystallinity has been reduced or (ii) pulp having high crystallinity is suitably used as a raw material cellulose.

Hereinafter, production methods involving using the items (i) and (ii) are sequentially described.

Production of C-HPC involving using (i) low-crystalline and powdery cellulose (Preparation of Low-Crystalline and Powdery Cellulose)

The low-crystalline and powdery cellulose to be used in this production method can be prepared from sheet- or roll-shaped pulp having a high cellulose purity obtained as a general-purpose raw material. A method of preparing the low-crystalline and powdery cellulose is not particularly limited. Examples thereof can include methods described in JP-A-62-236801, JP-A-2003-64184, and JP-A-2004-331918. Of those, a low-crystalline or amorphous and powdery cellulose (hereinafter sometimes collectively referred to as "low-crystalline and powdery cellulose") obtained through a mechanochemical treatment is more preferably used.

Here, the term "low-crystalline" in the low-crystalline and powdery cellulose means a state where the ratio of an amorphous moiety is larger in the crystal structure of the cellulose. Specifically, a powdery cellulose having a degree of crystallinity based on the following equation (31) of preferably 30% or less, more preferably 20% or less, even more preferably 10% or less is used. In particular, a completely amorphized cellulose the degree of crystallinity of which is substantially 0% is most preferably used.

$$\text{Degree of crystallinity (\%)} = [(I_{22.6} - I_{18.5})/I_{22.6}] \times 100 \quad (31)$$

In the equation (31), $I_{22.6}$ represents the diffraction intensity of a lattice plane (002 plane) in X-ray diffraction (diffraction angle 2θ=22.6°) and $I_{18.5}$ represents the diffraction intensity of the amorphous moiety (diffraction angle 2θ=18.5°).

A method of producing the low-crystalline and powdery cellulose based on the mechanochemical treatment is, for example, a method involving treating chip-shaped pulp, which is obtained by coarsely pulverizing sheet-shaped pulp, with a pulverizer. The chip-shaped pulp can be treated with an extruder before the treatment with the pulverizer.

The extruder to be used in the method is, for example, a uniaxial or biaxial extruder, preferably a biaxial extruder. An extruder having the so-called kneading disc portion at any portion of a screw is preferred from the viewpoint of applying a strong compression shear force.

A treatment method involving using the extruder, which is not particularly limited, is preferably a method involving loading the chip-shaped pulp into the extruder and continuously treating the pulp.

Examples of the pulverizer include: roll mills such as a high-pressure compression roll mill and a roll rotation mill; vertical roller mills such as a ring roller mill, a roller race mill, and a ball race mill; container-driving medium mills such as a rolling ball mill, a vibrating ball mill, a vibrating rod mill, a vibrating tube mill, a planetary ball mill, and a centrifugal fluid mill; medium-stirring mills such as a tower mill, a stirring tank mill, a flowing tank mill, and an annular mill; consolidation shearing mills such as a high-speed centrifugal roller mill and an ang mill; mortars; and stone grist mills. Of those, container-driving medium mills and medium-stirring mills are preferred, container-driving medium mills are more preferred, vibrating mills such as a vibrating ball mill, a vibrating rod mill, and a vibrating tube mill are even more preferred, and a vibrating ball mill and a vibrating rod mill are even more preferred from the viewpoints of an efficient crystallinity reduction and productivity.

Any one of a batch-type treatment method and a continuous treatment method is permitted.

Although a suitable range of the filling factor of a medium such as a ball or a rod varies depending on the model of the pulverizer, the filling factor falls within the range of preferably from 10 to 97%, more preferably from 15 to 95%. With such filling factor, the frequency at which the raw material pulp and the medium are brought into contact with each other increases, and an improving effect on pulverization efficiency can be significantly obtained without the inhibition of the movement of the medium.

Here, the filling factor refers to the apparent volume of the medium with respect to the capacity of the stirring portion of the pulverizer.

In the case of a ball mill, a material for the ball to be used as the medium is not particularly limited, and examples thereof include iron, stainless steel, alumina, and zirconia. The outer diameter of the ball is preferably from 0.1 to 100 mm, more preferably from 1 to 50 mm from the viewpoint of efficiently reducing the crystallinity of the cellulose.

In addition, a time for the treatment with the pulverizer is preferably from 5 minutes to 72 hours, more preferably from 10 minutes to 30 hours from the viewpoint of efficiently reducing the degree of crystallinity of the cellulose. In addition, the pulverizer treatment is desirably performed in the temperature range of preferably 250° C. or less, more preferably from 5 to 200° C. from the viewpoint of minimizing modification or deterioration due to heat generated during the treatment.

The rod to be used as the medium of the pulverizer is a rod-shaped medium, and a rod whose section is, for example, a polygon such as a tetragon or a hexagon, a circle, or an ellipse can be used.

The outer diameter of the rod falls within the range of preferably from 0.5 to 200 mm, more preferably from 1 to 100 mm, even more preferably from 5 to 50 mm. The length of the rod is not particularly limited as long as the length is shorter than the length of the container of the pulverizer. As long as the dimensions of the rod fall within the ranges, a desired pulverizing force is obtained and the cellulose can be reduced in crystallinity in an additionally efficient manner.

Although a time for a treatment with a vibrating mill filled with the rod and a temperature for the treatment are not particularly limited, the treatment can be performed for the same treatment time at the same treatment temperature as those of the ball mill.

The above described method enables molecular weight control, and enables easy preparation of a powdery cellulose having a high degree of polymerization and low crystallinity that is generally difficult to obtain.

The average degree of polymerization of the low-crystalline andpowdery cellulose is preferably from 100 to 2,000, more preferably from 300 to 1,500, even more preferably from 350 to 1,350.

In addition, the average particle diameter of the low-crystalline and powdery cellulose is not particularly limited because the cellulose has only to maintain a state with good flowability as powder. The average particle diameter is preferably 300 μm or less, more preferably 150 μm or less, even more preferably 50 μm or less. It should be noted that the average particle diameter of the low-crystalline and powdery cellulose is preferably 20 μm or more, more preferably 25 μm or more from the viewpoint of an improvement in handleability of the powdery cellulose. However, an undersize product obtained with a sieve having an aperture of about from 300 to 1,000 μm is preferably used in the reaction as required for avoiding the inclusion of a trace amount of coarse particles due to agglomeration or the like.

(Cationization of Low-Crystalline and Powdery Cellulose)

The low-crystalline and powdery cellulose obtained as described above is cationized through a reaction with a glycidyl trialkylammonium salt in the presence of a base to produce a cationized cellulose.

Examples of the glycidyl trialkylammonium salt to be used as a cationizing agent include glycidyl trimethylammonium chloride, glycidyl triethylammonium chloride, glycidyl trimethylammonium bromide, and glycidyl triethylammonium-bromide. Of those, glycidyl trimethylammonium chloride is preferred from the viewpoint of availability.

The addition amount of the glycidyl trialkylammonium salt is preferably from 0.01 to 3.0 times mole, more preferably from 0.02 to 2 times mole, even more preferably from 0.04 to 1.0 time mole with respect to 1 mole of the anhydroglucose unit of the cellulose in ordinary cases from the viewpoints of: good foaming; excellent rinse-off characteristics; effective suppression of the entanglement of hair, and the volume of hair, after drying even when hair is damaged hair; and the impartment of bounce and resilience to hair.

Examples of the base that is caused to be present at the time of the cationization include lithium hydroxide, sodium hydroxide, potassium hydroxide, calcium hydroxide, and barium hydroxide. Of those, sodium hydroxide and barium hydroxide are more preferred from the viewpoints of availability, general versatility, and economic efficiency. The addition amount of the base, which varies depending on, for example, the kind of the cellulose, is preferably from 0.05 to 1.0 time mole, more preferably from 0.1 to 0.5 time mole, even more preferably from 0.2 to 0.3 time mole with respect to 1 mole of the anhydroglucose unit of the cellulose in ordinary cases.

A water content in the reaction system is preferably 100 mass % or less with respect to the cellulose used as a raw material. With such water content, excessive agglomeration of the cellulose is suppressed and the cellulose can be caused to react in a powdery state with flowability. From the viewpoint, the content is more preferably 80% by mass or less, even more preferably from 5 to 50% by mass.

A temperature for the reaction is preferably from 10 to 85° C., more preferably from 15 to 80° C. in ordinary cases.

(Hydroxypropylation of Cationized Cellulose)

The C-HPC can be produced by hydroxypropylating the cationized cellulose thus obtained through its reaction with propylene oxide.

Here, the usage of propylene oxide is preferably from 0.01 to 5.0 times mole, more preferably from 0.1 to 3.0 times mole per 1 mole of the anhydroglucose unit in the cellulose molecule from the viewpoints of: good foaming; excellent rinse-off characteristics; effective suppression of the entanglement of hair, and the volume of hair, after drying even when hair is damaged hair; and the impartment of bounce and resilience to hair.

A base or acid may be used as a catalyst for the hydroxypropylation.

Of those, examples of the base catalyst include: alkali metal hydroxides such as sodium hydroxide, potassium hydroxide, and lithium hydroxide; alkaline earth metal hydroxides such as magnesium hydroxide and calcium hydroxide; and tertiary amines such as trimethylamine, triethylamine, and triethylenediamine.

In addition, examples of the acid catalyst include Lewis acid catalysts such as lanthanide triflates.

Of those, from the viewpoint of suppressing a reduction in degree of polymerization of the raw material cellulose, a base catalyst is preferred, an alkali metal hydroxide is more preferred, and sodium hydroxide or potassium hydroxide is even more preferred. One kind of those catalysts can be used alone, or two or more kinds thereof can be used in combination.

The usage of the catalyst, which is not particularly limited, is preferably from 0.05 to 1.0 time mole, more preferably from 0.1 to 0.8 time mole, even more preferably from 0.2 to 0.5 time mole per 1 mole of the anhydroglucose unit in the cellulose molecule in ordinary cases.

A method of adding propylene oxide is not particularly limited, and examples thereof include: a method involving adding the catalyst to the cationized cellulose and then dropping propylene oxide; and a method involving collectively adding propylene oxide to the cationized cellulose and then gradually adding the catalyst to perform the reaction.

A water content in the reaction system is preferably 100% by mass or less with respect to the cellulose used as a raw material. As long as the water content with respect to the cellulose falls within the range, the cationized cellulose does not excessively agglomerate and hence the cellulose can be caused to react in a powdery state with flowability. From the viewpoint, the content is preferably 80% by mass or less, more preferably from 5 to 50% by mass.

In the present invention, the cationized cellulose, the catalyst, and propylene oxide are preferably caused to react with one another in powdery states with flowability. Alternatively, the following is permitted. The cationized cellulose powder and the catalyst are uniformly mixed and dispersed with, for example, a mixing machine such as a mixer, a shaker, or a mixing mill in advance as required, and then propylene oxide is added and caused to react with the resultant.

A reaction temperature for the hydroxypropylation is preferably from 0 to 150° C. From the viewpoints of avoiding the polymerization of the molecules of propylene oxide and avoiding abrupt occurrence of the reaction, the temperature is more preferably from 10 to 100° C., even more preferably from 20 to 80° C. The reaction can be performed at normal pressure.

In addition, the reaction is preferably performed under an inert gas atmosphere such as nitrogen from the viewpoint of avoiding a molecular weight reduction due to the cleavage of the cellulose chain during the reaction.

After the completion of the reaction, unreacted propylene oxide is removed and then a neutralization treatment, a purification treatment, or the like is performed as required, followed by drying. Thus, the C-HPC of the present invention can be obtained.

The neutralization treatment can be performed by an ordinary method. For example, when a base catalyst is used as the catalyst, the treatment can be performed by adding an acid liquid such as acetic acid, a mixed solution of an acid and an inert organic solvent, or an aqueous solution of an acid. The kind of the acid is not particularly limited and has only to be appropriately selected in consideration of, for example, the corrosion of an apparatus. The purification treatment can be performed by means of: washing with a solvent such as hydrous isopropanol or a hydrous acetone solvent and/or water; or a dialysis membrane.

The method of producing the C-HPC involving using (i) the low-crystalline and powdery cellulose has been described above. With regard to the order in which the reactions of the cationization and the hydroxypropylation are performed in the production method, the cationization may be performed after the hydroxypropylation of the raw material cellulose has been performed, or the cationization and the hydroxypropylation may be simultaneously performed.

In addition, substantially no cleavage of a cellulose skeleton serving as the main chain occurs in the cationization reaction step and hydroxypropylation reaction step in the method of producing the C-HPC involving using (i) the low-crystalline and powdery cellulose. Accordingly, the average degree of polymerization of the C-HPC to be obtained can be approximated to the average degree of polymerization of the powdery cellulose after the crystallinity reduction treatment.

Production of C-HPC Involving Using (II) Pulp Having High Crystallinity (Cationization of Pulp)

In this production method, the pulp having high crystallinity is used as the raw material cellulose without the use of the low-crystalline and powdery cellulose. In this case, a crystallinity reduction is preferably performed upon cationization for improving the reactivity of the pulp.

Specifically, the cationized cellulose can be obtained by: adding a cationizing agent to the pulp, performing a crystallinity reduction through a pulverizer treatment, adding a base to the resultant, and performing a reaction between the pulp and the cationizing agent while performing a crystallinity reduction through a pulverizer treatment; or adding the base to the pulp, performing a crystallinity reduction through a pulverizer treatment, adding the cationizing agent to the resultant, and performing a reaction between the pulp and the cationizing agent while performing a crystallinity reduction through a pulverizer treatment.

From the viewpoint of the solubility of the C-HPC to be obtained through the cationization in water, in the cationization of the cellulose, the following is preferred. First, the cationizing agent is added to the pulp, a crystallinity reduction is performed through a pulverizer treatment, the base is added to the resultant, and the reaction between the pulp and the cationizing agent is performed while a crystallinity reduction is performed through a pulverizer treatment.

The shape of the pulp to be used as the raw material cellulose is not particularly limited as long as the pulp can be introduced into a production apparatus without a hitch. From an operational viewpoint, sheet-shaped pulp, pellet- or chip-shaped pulp obtained by cutting or coarsely pulverizing the sheet-shaped pulp, or a powdery cellulose obtained by finely pulverizing the sheet-shaped pulp is preferably used.

The degree of crystallinity of the pulp to be used as the raw material cellulose is not limited. However, a treatment for reducing the degree of crystallinity of the cellulose typically involves a molecular weight reduction in association with the cleavage of the cellulose chain. Accordingly, a cellulose showing a small molecular weight reduction and having additionally high crystallinity is preferably used for obtaining a cationized cellulose having an additionally high molecular weight. In addition, in contrast, a cellulose having an extremely high degree of crystallinity, specifically, a degree of crystallinity represented by the equation (31) in excess of 95% is difficult to obtain. Accordingly, the degree of crystallinity of the raw material cellulose represented by the equation (31) is preferably from 10 to 95%, more preferably from 30 to 90%, even more preferably from 60 to 80% from the viewpoints of a degree of polymerization and availability.

Although the average degree of polymerization of the raw material cellulose is also not limited, a raw material cellulose having an additionally large degree of polymerization is preferably used for obtaining a cationized cellulose having an additionally high molecular weight. From the viewpoint, the average degree of polymerization of the raw material cellulose is preferably from 100 to 2,000, more preferably from 250 to 1,900, even more preferably from 350 to 1,800.

Preferred aspects of, for example, the kind and amount of the cationizing agent, the kind of the base, the kind of the pulverizer, and a method and conditions for the crystallinity reduction are in conformity with those described in the section "production of C-HPC involving using (i) low-crystalline and powdery cellulose" except the time for the treatment with the pulverizer for the crystallinity reduction and the amount of the base.

The time for the treatment with the pulverizer for the crystallinity reduction is preferably from 1 minute to 5 hours, more preferably from 2 minutes to 3 hours, even more preferably from 5 minutes to 2 hours.

In addition, when the addition amount of the base is 0.01 equivalent or more per 1 mole of the anhydroglucose unit of the raw material cellulose, the reaction between the cellulose and the cationizing agent rapidly progresses, and when the addition amount is 1 equivalent or less, the yield of the reaction between the cellulose and the cationizing agent is high. From the viewpoint, the addition amount of the base is preferably from 0.05 to 0.8 equivalent, more preferably from 0.1 to 0.7 equivalent, even more preferably from 0.2 to 0.6 equivalent per 1 mole of the anhydroglucose unit of the raw material cellulose.

In addition, the cationization progresses at the time of the crystallization reduction after the addition of the cationizing agent and the base. When the reaction is insufficient, the reaction can be advanced by performing aging at preferably from 10 to 100° C., more preferably from 30 to 80° C.

A water amount at the time of the aging and a preferred aspect thereof are in conformity with those in the case of the cationization of the low-crystalline and powdery cellulose as described above except that the pulp is used instead of the low-crystalline and powdery cellulose as a raw material.

In addition, the reaction is preferably performed under an inert gas atmosphere such as nitrogen from the viewpoint of avoiding a molecular weight reduction due to the cleavage of the cellulose chain during the reaction.

(Hydroxypropylation of Cationized Cellulose)

The amount of propylene oxide used in the hydroxypropylation of the cationized cellulose in the production of the C-HPC involving using (ii) the pulp having high crystallinity, a catalyst, reaction conditions, a treatment after the completion of the reaction, and preferred aspects thereof are in conformity with those described in the hydroxypropylation in the production of the C-HPC involving using (i) the low-crystalline and powdery cellulose.

A method of producing a C-HPC involving using (ii) pulp having high crystallinity, in which a crystallinity reduction is performed upon cationization and the resultant cationized cellulose is subjected to hydroxypropylation, is preferred as the method of producing the C-HPC to be employed in the present invention from the viewpoints of: good foaming; excellent rinse-off characteristics; effective suppression of the entanglement of hair, and the volume of hair, after drying even when hair is damaged hair; and impartment of bounce and resilience to hair.

(Component (C): Organic Solvent)

The component (C) is one or two or more organic solvents selected from the group consisting of the following components (C1) and (C2):

(C1) an aromatic alcohol represented by the following general formula (4):

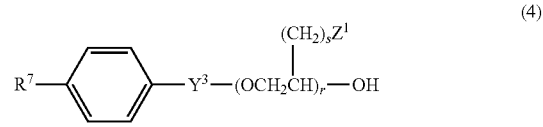

wherein, in the general formula (4), $R^7$ represents a hydrogen atom, a methyl group, or a methoxy group, $Y^3$ represents a single bond, or a linear or branched alkylene group or alkenylene group having from 1 to 3 carbon atoms, $Z^1$ represents a hydrogen atom or a hydroxyl group, and r and s each represent a number of from 0 to 5; and (C2) a polypropylene glycol having a molecular weight of from 200 to 1,000.

One kind of those components (C) can be used alone, or two or more kinds thereof can be used in combination.

Of those, examples of the aromatic alcohol as the component (C1) include benzyl alcohol, cinnamyl alcohol, phenethyl alcohol, p-anisyl alcohol, p-methylbenzyl alcohol, phenoxyethanol, and 2-benzyloxyethanol. Of those, benzyl alcohol and 2-benzyloxyethanol are more preferred.

In addition, it is preferred to use, as the component (C), one or more kinds selected from the group consisting of benzyl alcohol, 2-benzyloxyethanol, and a polypropylene glycol having a molecular weight of from 200 to 700.

The content of the component (C) in terms of the total of the components (C1) and (C2) is preferably 0.01% by mass or more, more preferably 0.05% by mass or more, even more preferably 0.1% by mass or more with respect to the entirety of the aqueous hair cleansing composition from the viewpoints of: good flexibility at the time of use; effective suppression of the entanglement of hair, and the volume of hair, after drying; and impartment of bounce and resilience, and luster to hair. In addition, the content of the component (C) in terms of the total of the components (C1) and (C2) is preferably 20% by mass or less, more preferably 10% by mass or less, even more preferably 5% by mass or less with respect to the entirety of the aqueous hair cleansing composition from the viewpoints of improving the rinse-off characteristics of hair and suppressing a residual feeling in rinsing.

In addition, the mass ratio (component (B)/component (C)) of the component (B) to the component (C) in the aqueous hair cleansing composition of the present invention is preferably 0.01 or more, more preferably 0.02 or more, even more preferably 0.04 or more from the viewpoints of: good foaming; excellent rinse-off characteristics; and effective suppression of the entanglement of hair, and the volume of hair, after drying even when hair is damaged hair. In addition, the ratio "component (B)/component (C)" in the aqueous hair cleansing composition of the present invention is preferably 5 or less, more preferably 3 or less, even more preferably 1.5 or less from the viewpoint of a balance between good foaming and a suppressing effect on the entanglement of hair after drying and at the time of rinsing.

(Component (D): Organic Carboxylic Acid)

The component (D) is one or two or more organic carboxylic acids selected from the group consisting of a hydroxy monocarboxylic acid and a dicarboxylic acid. Specific examples of the hydroxy monocarboxylic acid include glycolic acid, lactic acid, glyceric acid, gluconic acid, and pantothenic acid. Specific examples of the dicarboxylic acid include malic acid, oxalic acid, malonic acid, maleic acid, succinic acid, and glutaric acid. Of those, glycolic acid, lactic acid, malic acid, and tartaric acid are preferred, and one or more kinds selected from the group consisting of glycolic acid, lactic acid, and malic acid are more preferred from the viewpoint of improving foaming under an acidic condition by using the components (A), (B), and (C) in combination.

The content of such component (D) is preferably 0.3% by mass or more, more preferably 0.5% by mass or more, even more preferably 0.7% by mass or more with respect to the entirety of the aqueous hair cleansing composition of the present invention from the viewpoint of an improvement in finish feeling of hairs such as luster or settlement after drying. In addition, the content of the component (D) is preferably 5% by mass or less, more preferably 3% by mass or less, even more preferably 2% by mass or less with respect to the entirety of the aqueous hair cleansing composition of the present invention from the viewpoint of foam quality.

(pH)

The aqueous hair cleansing composition of the present invention has a pH of from 2 to 5 at 25° C. when diluted 20-fold by mass with water. When the components (A) to (D) are used in combination and the pH of the composition is set to the foregoing value, the entanglement of hair, and the volume of hair, after drying can be suppressed, and hair luster and settlement can be improved. From the viewpoint, the pH at 25° C. when the aqueous hair cleansing composition of the present invention is diluted 20-fold by mass with water is preferably from 2.5 to 4.5, more preferably from 3 to 4.5.

(Preferred Content of Each Component)

With regard to the formulation of the components (A) to (D) in the aqueous hair cleansing composition of the present invention, it is preferred that the content of the component (A) be from 5 to 18% by mass, the content of the component (B) be from 0.02 to 5% by mass, the content of the component (C) be from 0.05 to 10% by mass, and the content of the component (D) be from 0.5 to 3% by mass.

In addition, the content of water in the aqueous hair cleansing composition of the present invention is preferably 50% by mass or more and more preferably 60% by mass or more preferably 95% by mass or less and more preferably 90% by mass or less.

Next, a method of producing the aqueous hair cleansing composition in the present invention is described.

The method of producing the aqueous hair cleansing composition in the present invention, which is not particularly limited, includes, for example, the steps of: obtaining the cationized hydroxypropyl cellulose as the component (B) according to the method including the first and second steps; and mixing the component (B) obtained in the foregoing step, the component (A), the component (C), the component (D), and water.

(Action)

In the aqueous hair cleansing composition of the present invention, the foregoing components (A) to (D) are used in combination. Accordingly, the composition foams well, is excellent in rinse-off characteristics, and is effective in suppressing the entanglement of hair, and the volume of hair, after drying even when hair is damaged hair. Although the reason for the foregoing is not necessarily clear, the following assumption has been made: the component (A) and the component (B) coacervate at the time of rinsing to deposit a composite on the surface of hair, and hence the component (B) becomes able to remain even after the rinsing. In addition, the component (B) on the surface of hair, and the component (A), the component (C), and the component (D) create foam quality suitable for hair washing. Accordingly, even when the composition is applied to damaged hair, the composition is excellent in functions as a cleansing composition. Specifically, the composition has good foamingproperty, is excellent in rinse-off characteristics, and suppresses the entanglement of hair, and the volume of hair, after drying.

(Other Components)

The aqueous hair cleansing composition of the present invention may contain components except the components (A) to (D) and water.

For example, the aqueous hair cleansing composition of the present invention may be constructed so as to contain a cationized polymer except the component (B). Examples of the cationized polymer except the component (B) include: cationized cellulose derivatives such as a cationized hydroxyethyl cellulose; cationic starches; cationized galactomannans such as cationized fenugreek gum, cationized guar gum, cationized tara gum, and cationized locust bean gum, and derivatives thereof; copolymers such as a diallyl quaternary ammonium salt/acrylamide copolymer, a vinylimidazolium trichloride/vinylpyrrolidone copolymer, a hydroxyethyl cellulose/dimethyldiallylammonium chloride copolymer, a vinylpyrrolidone/quaternized dimethylaminoethyl methacrylate copolymer, a polyvinylpyrrolidone/alkylamino acrylate copolymer, a polyvinylpyrrolidone/alkylamino acrylate/vinylcaprolactam copolymer, a vinylpyrrolidone/methacrylamidopropyltrimethylammonium chloride copolymer, an alkyl acrylamide/acrylate/alkylaminoalkyl acrylamide/polyethylene glycol methacrylate copolymer, and an adipic acid/dimethylaminohydroxypropylethylenetriamine copolymer (manufactured by Sandoz, US, Cartaretin); a cationic polymer disclosed in JP-A-53-139734; and a cationic polymer disclosed in JP-A-60-36407.

Of those, one or more kinds selected from the group consisting of cationized guar gum, cationized tara gum, and cationized hydroxyethyl cellulose are preferably used from the viewpoint of reducing the stickiness and coarse feeling of hair at the time of rinsing.

Of those, cationized galactomannan is a water-soluble cationized polymer obtained by introducing a quaternary nitrogen-containing group to a galactomannan whose main chain consists of mannose as a constituent unit and that consists of a galactose unit as a side chain. The galactomannan is, for example, obtained from the endosperm of the seeds of a leguminous plant. Galactomannans having ratios between galactose and mannose of 1:1, 1:2, 1:3, and 1:4 are fenugreek gum, guar gum, tara gum, and locust bean gum, respectively.

Commercially available products of the cationized galactomannan are shown below. As a commercially available product of the cationized fenugreek gum, there is given Catinal CF-100 (manufactured by TOHO CHEMICAL INDUSTRY Co., Ltd.). As a commercially available product of the cationized guar gum, there are given, for example, JAGUAR series such as JAGUAR C-13S, JAGUAR C-14S, and JAGUAR C-17 (manufactured by Rhodia, guar hydroxypropyltrimonium chloride). In addition, as a commercially available product of the cationized tara gum, there are given, for example, Catinal CTR-100 and Catinal CTR-200 (manufactured by TOHO CHEMICAL INDUSTRY Co., Ltd.). In addition, as a commercially available product of the cationized locust bean gum, there is given, for example, Catinal CLB-100 (manufactured by TOHO CHEMICAL INDUSTRY Co., Ltd., locust bean hydroxypropyltrimonium chloride).

In addition, as other commercially available products that may be used as the cationized polymer except the component (B), there are given, for example, MERQUAT 550 (manufactured by NALCO, a copolymer of acrylamide and a diallyldimethylammonium salt; INCI name: polyquaternium-7), Luviquat FC370 (manufactured by BASF, a copolymer of 1-vinyl-2-pyrrolidone and a 1-vinyl-3-methylimidazolium salt; INCI name: polyquaternium-16), Gafquat 755N (manufactured by ISP, a copolymer of 1-vinyl-2-pyrrolidone and dimethylaminoethyl methacrylate; INCI name: polyquaternium-11), Ucare Polymer JR and Ucare Polymer LR series (manufactured by Amerchol, a salt of a reaction product of an trimethylammonium-substituted epoxide and a hydroxyethyl cellulose; INCI name:polyquaternium-10), and POIZC-60H, POIZC-80M, and POIZ C-150L (each of which is manufactured by Kao Corporation and is a salt of a reaction product of a trimethylammonium-substituted epoxide and a hydroxyethyl cellulose; INCI name: polyquaternium-10).

Two or more kinds of cationized polymers except the component (B) may be used in combination, and their content can be set to, for example, from 0.01 to 3% by mass with respect to the entirety of the aqueous hair cleansing composition of the present invention from the viewpoint of reducing the coarse feeling of hair at the time of rinsing. The content is preferably from 0.02 to 2% by mass, more preferably from 0.05 to 1% by mass.

A nonionic surfactant or an amphoteric surfactant may be incorporated into the aqueous hair cleansing composition of the present invention for additionally improving its cleaning performance.

Examples of the nonionic surfactant include polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers such as polyoxyethylene (6) stearyl ether, polyoxyalkylene alkyl phenyl ethers, polyoxyalkylene (hydrogenated) castor oils, sucrose fatty acid esters, polyglycerol alkyl ethers, polyglycerol fatty acid esters, fatty acid alkanolamides, alkyl glycosides, monoalkyl gylceryl ethers such as isodecyl glyceryl ether, and monoalkenyl gylceryl ethers.

Of those, polyoxyalkylene sorbitan fatty acid esters such as a polyoxyethylene sorbitan fatty acid ester, polyoxyalkylene fatty acid esters such as a polyoxyalkylene (C8 to 20) fatty acid ester, polyoxyalkylene (hydrogenated) castor oils such as a polyoxyethylene hydrogenated castor oil, and alkyl glycosides are preferred.

In addition, a fatty acid alkanolamide is also suitable, may be any of a monoalkanolamide and a dialkanolamide, and is preferably one having an acyl group with from 8 to 18 carbon atoms, more preferably one having an acyl group with from 10 to 16 carbon atoms. In addition, one having a hydroxyalkyl group with 2 or 3 carbon atoms is preferred, and examples thereof include oleic acid diethanolamide, palm kernel oil fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide, and lauric acid monoethanolamide.

Examples of the amphoteric surfactant include betaine-based surfactants. Of those, an alkyldimethylamino acetic acid betaine, a fatty acid amide propylbetaine, an alkyl hydroxy sulfobetaine, and the like are preferred. Of those, a fatty acid amide propylbetaine is preferred. The fatty acid amide propylbetaine is preferably one having an acyl group with from 8 to 18 carbon atoms, more preferably one having an acyl group with from 10 to 16 carbon atoms. Of those, lauramidopropyl betaine, palm kernel oil fatty acid amide propylbetaine, coconut oil fatty acid amide propylbetaine, and the like are preferred.

In addition, as other amphoteric surfactants, there are given sultaine-based surfactants such as lauryl hydroxysultaine.

One kind of those nonionic surfactants or amphoteric surfactants can be used alone in the aqueous hair cleansing composition, or two or more kinds thereof can be used in combination. When the aqueous hair cleansing composition of the present invention is of the form of an aqueous liquid cleansing composition, the use of a fatty acid amide propylbetaine, a fatty acid alkanolamide, or a monoalkyl glyceryl ether together with the component (A) not only additionally improves the foaming force of the composition but also provides moderate liquid property.

The content of the nonionic surfactant or the amphoteric surfactant is preferably from 0.01 to 15% by mass, more preferably from 0.05 to 8% by mass, even more preferably from 0.1 to 6% by mass with respect to the entirety of the aqueous hair cleansing composition of the present invention from such a viewpoint that a good foam-increasing effect is obtained.

The aqueous hair cleansing composition of the present invention can be further blended with a cationic surfactant or silicones for improving finish feeling after drying.

Examples of the cationic surfactant include (i) an alkyltrimethylammonium salt, (ii) an alkoxytrimethylammonium salt, (iii) a dialkyldimethylammonium salt, (iv) an alkyldimethylamine and a salt thereof, (v) an alkoxydimethylamine and a salt thereof, and (vi) an alkylamidodimethylamine and a salt thereof.

(i) Alkyltrimethylammonium Salt

Examples of the alkyltrimethylammonium salt include one represented by the following general formula.

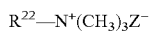

In the formula, $R^{22}$ represents an alkyl group having from 12 to 22 carbon atoms, and $Z^-$ represents a halide ion such as a chloride ion or a bromide ion.

Further, specific examples thereof include cetyltrimethylammonium chloride, stearyltrimethylammonium chloride, and behenyltrimethylammonium chloride.

(ii) Alkoxytrimethylammonium Salt

Examples of the alkoxytrimethylammonium salt include one represented by the following general formula.

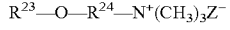

In the formula, $R^{23}$ represents an alkyl group having from 12 to 22 carbon atoms, $R^{24}$ represents an ethylene group or propylene group that may be substituted by a hydroxy group, and $Z^-$ represents the same as described above.

Further, specific examples thereof include stearoxypropyltrimethylammonium chloride, stearoxyethyltrimethylammonium chloride, and stearoxyhydroxypropyltrimethylammonium chloride.

(iii) Dialkyldimethylammonium Salt

Examples of the dialkyldimethylammonium salt include one represented by the following general formula.

$(R^{25})_2N^+(CH_3)_2Z^-$

In the formula, $R^{25}$'s each independently represent an alkyl group having from 12 to 22 carbon atoms or an benzyl group, and $Z^-$ represents the same as described above.

Further, specific examples thereof include distearyldimethylammonium chloride.

(Iv) Alkyldimethylamine and Salt Thereof.

Examples of the alkyldimethylamine and the salt thereof include one represented by the following general formula and a salt thereof.

$R^{26}-N(CH_3)_2$

In the formula, $R^{26}$ represents an alkyl group having from 12 to 22 carbon atoms.

Further, specific examples thereof include behenyldimethylamine, stearyldimethylamine, and organic acid salts thereof.

(v) Alkoxydimethylamine and Salt Thereof.

Examples of the alkoxydimethylamine and the salt thereof include one represented by the following general formula and a salt thereof.

$R^{27}-O-R^{28}-N(CH_3)_2$

In the formula, $R^{27}$ represents an alkyl group having from 12 to 22 carbon atoms, and $R^{28}$ represents an ethylene group or a propylene group.

(Vi) Alkylamidodimethylamine and Salt Thereof.

Examples of the alkylamidodimethylamine and the salt thereof include one represented by the following general formula and a salt thereof.

$R^{29}-C(=O)NH-R^{30}-N(CH_3)_2$

In the formula, $R^{29}$ represents an alkyl group having from 11 to 21 carbon atoms, and $R^{30}$ represents an ethylene group or a propylene group.

Examples of the cationic surfactant except the above-mentioned (i) to (vi) include: a lanolin fatty acid aminopropylethyldimethylammonium ethyl sulfate (ethyl sulfate of an alkanoylaminopropyldimethylethylammonium, the alkanoyl group is derived from lanolin), a lanolin fatty acid aminoethyltriethylammonium ethyl sulfate, a lanolin fatty acid aminopropyltriethylammonium ethyl sulfate, a lanolin fatty acid aminoethyltrimethylammonium methyl sulfate, a lanolin fatty acid aminopropylethyldimethylammonium methyl sulfate, an isoalkanoic acid (C14 to 20) aminopropylethyldimethylammonium ethyl sulfate, an isoalkanoic acid (C18 to 22) aminopropylethyldimethylammonium ethyl sulfate, isostearic acid aminopropylethyldimethylammonium ethyl sulfate, isononanoic acid aminopropylethyldimethylammonium ethyl sulfate, and an alkyltrimethylammonium saccharin.

Two or more kinds of the cationic surfactants may be used in combination, and their content in the aqueous hair cleansing composition of the present invention is preferably from 0.01 to 10% by mass, more preferably from 0.02 to 6% by mass, even more preferably from 0.05 to 3% by mass in terms of smoothness during a time period commencing on hair washing and ending on rinsing.

Examples of the silicones include the following silicones.
(I) Dimethylpolysiloxane

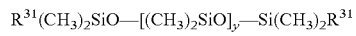

$R^{31}(CH_3)_2SiO-[(CH_3)_2SiO]_y-Si(CH_3)_2R^{31}$

In the formula, $R^{31}$'s each independently represents a methyl group or a hydroxy group, and y represents a number of from 1 to 20,000.

Dispersed particles of dimethylpolysiloxane each have an average particle diameter of preferably less than 100 μm, more preferably 50 μm or less, even more preferably 4 μm or less, even more preferably 2 μm or less. In addition, the average particle diameter is preferably 0.1 μm or more from the viewpoints of sense of use and a conditioning effect.

As such dimethylpolysiloxane, for example, there may be used: a product commercially available under the name "Silicone CF2450" from Toray Dow Corning containing dimethylpolysiloxane oil represented by the above-mentioned formula where y represents from 300 to 6,500 at 60% by mass and having an average particle diameter of 0.8 μm; or a product commercially available under the name "Silicone CF2460" from Toray Dow Corning or under the name "KHE-1" from Shin-Etsu Chemical Co., Ltd. containing dimethylpolysiloxane oil represented by the above-mentioned formula where y represents from 300 to 6,500 at 50% by mass and having an average particle diameter of 50 μm.

(II) Amino-modified Silicone

Any of various amino-modified silicones may be used, and the silicone disclosed in the third edition of the CTFA dictionary (United States of America, Cosmetic Ingredient Dictionary) under the name of amodimethicone and having an average molecular weight of about from 3,000 to 100,000 is more preferred. As a commercially available product thereof, there are given, for example, SM8704C (manufactured by Toray Dow Corning), DC929 (manufactured by Dow Corning), KT1989 (manufactured by Momentive Performance Materials Inc.), 8500 Conditioning Agent, DOW CORNING TORAY SS-3588, and DOW CORNING TORAY SILSTYLE 104 (manufactured by Toray Dow Corning).

(III) Other Silicones

In addition to the above-mentioned silicones, there are given, for example, a polyether-modified silicone, a methylphenylpolysiloxane, a fatty acid-modified silicone, an alcohol-modified silicone, an alkoxy-modified silicone, an epoxy-modified silicone, a fluorine-modified silicone, a cyclic silicone, and an alkyl-modified silicone.

Two or more kinds of those silicones may be used in combination, and their content in the aqueous hair cleansing composition of the present invention is preferably from 0.01 to 10% by mass, more preferably 0.05 to 5% by mass, even more preferably 0.1 to 3% by mass in terms of smoothness during a time period commencing on hair washing and ending on rinsing.

The aqueous hair cleansing composition of the present invention may further contain a pearling agent containing an ethylene glycol monofatty acid ester, an ethylene glycol difatty acid ester, an ethylene glycol monoalkyl ether, or an ethylene glycol dialkyl ether.

Examples of the ethylene glycol monofatty acid ester include ethylene glycol monostearic acid ester and ethylene glycol monobehenic acid ester, and examples of the ethylene glycol difatty acid ester include ethylene glycol distearyl ester (referred to as "ethylene glycol distearyl" in Examples (Table 3) to be described later), and ethylene glycol dibehenyl ester. Examples of the ethylene glycol monoalkyl ether include ethylene glycol monostearyl ether, and examples of the ethylene glycol dialkyl ether include ethylene glycol distearyl ether.

Two or more kinds of the foregoing may be used in combination, and their content in the aqueous hair cleansing composition of the present invention is preferably from 0.1 to 10% by mass, more preferably from 0.2 to 5% by mass, even more preferably from 0.5 to 4% by mass in terms of an improvement in storage stability of the aqueous hair cleansing composition, and an improvement in smoothness at the time of foaming and at the time of rinsing.

In addition, the aqueous hair cleansing composition of the present invention can contain an oil solution as another conditioning agent. Examples of the oil solution include: hydrocarbons such as squalene, squalane, liquid paraffin, liquid isoparaffin, and cycloparaffin; glycerides such as castor oil, cacao oil, mink oil, avocado oil, olive oil, sunflower oil, and camellia oil; waxes such as beeswax, spermaceti, lanolin, and carnauba wax; alcohols such as cetyl alcohol, oleyl alcohol, stearyl alcohol, isostearyl alcohol, 2-octyldodecanol, glycerin, myristyl alcohol, behenyl alcohol, and cetostearyl alcohol; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, a coconut oil fatty acid, isostearic acid, and isopalmitic acid; and isostearyl glyceryl ether and a polyoxypropylene butyl ether as well. Of those, higher alcohols are preferred, and myristyl alcohol, cetyl alcohol, stearyl alcohol, sunflower oil, and camellia oil are more preferred.

One kind of those oil solutions can be used alone, or two or more kinds thereof can be used in combination. Their content in the aqueous hair cleansing composition of the present invention is preferably from 0.001 to 2% by mass, more preferably from 0.005 to 1.5% by mass, even more preferably from 0.01 to 1% by mass.

The aqueous hair cleansing composition of the present invention may contain a viscosity modifier, and examples of the viscosity modifier include a hydroxyethyl cellulose, a methyl cellulose, a polyethylene glycol, ethylene glycol, propylene glycol, isoprene glycol, ethanol, clay minerals, and salts (such as sodium chloride, ammonium chloride, and sodium citrate). Of those, ethanol, sodium chloride, and sodium citrate are preferred. Two or more kinds of the viscosity modifiers may be used in combination, and their usage in the aqueous hair cleansing composition of the present invention is preferably from 0.01 to 5% by mass, more preferably from 0.05 to 4% by mass, even more preferably from 0.1 to 3% by mass in terms of a foam amount and foam quality.

The aqueous hair cleansing composition of the present invention can be appropriately blended with a component to be used in an ordinary aqueous hair cleansing composition depending on purposes in addition to the foregoing components. Examples of such arbitrary component include anti-dandruff agents, vitamin agents, germicides, anti-inflammatory agents (such as glycyrrhizic acid, glycyrrhetic acid, and derivatives thereof), antiseptic agents, chelating agents, moisturizing agents (such as sorbitol and panthenol), colorants (such as a dye and a pigment), extracts (such as a polar solvent extract of a eucalyptus, a protein obtained from a shell or pearl having nacre, or a hydrolysate thereof, honey, royal jelly, a protein obtained from silk or a hydrolysate thereof, a protein-containing extract obtained from the seeds of a leguminous plant, an Asian ginseng extract, a rice germ extract, a Fucus extract, an aloe extract, a lotus extract, a pomegranate extract, a wild rose extract, a chamomile extract, a licorice root extract, an Alpinia speciosa leaf extract, and a chlorella extract), pearling agents except the foregoing components such as titanium oxide, perfumes, UV absorbers, antioxidants, shea butter, rose water, orange oil, and eucalyptus oil. The aqueous hair cleansing composition of the present invention is produced by dissolving a mixture of the components (A) to (D) and any such other component in water.

The aqueous hair cleansing composition of the present invention may be blended with a pH adjustor except the component (D). Examples of such pH adjustor include organic acids except the component (D), and an aromatic carboxylic acid such as benzoic acid can also be used. In addition, a base such as sodium hydroxide, potassium hydroxide, or ammonium chloride may be used as another pH adjustor in combination with any such organic acid.

Although a liquid, a gel, or the like can be appropriately selected as the form of the aqueous hair cleansing composition of the present invention, a liquid agent using water or water and a lower alcohol as a solvent is preferred.

It should be noted that the present invention is not limited to the foregoing embodiments, and such modifications, improvements, and the like that an object of the present invention can be achieved are included in the present invention.

The embodiments of the present invention described above are collectively described below.

<1>

An aqueous hair cleanising composition, containing the following components (A), (B), (C), and (D), and water, in which the aqueous hair cleansing composition has a pH of from 2 to 5 at 25° C. when diluted 20-fold by mass with water:
(A) an anionic surfactant;
(B) a cationized hydroxypropyl cellulose having a main chain derived from an anhydroglucose represented by the following general formula (1), and having a degree of substitution with cationized ethyleneoxy groups of from 0.01 to 2.9 and a degree of substitution with propyleneoxy groups of from 0.1 to 4.0:

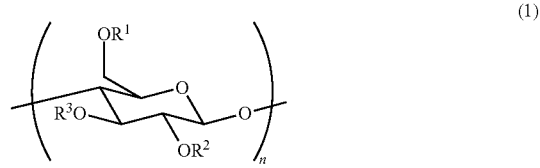

wherein, in the general formula (1), $R^1$, $R^2$, and $R^3$ each independently represent a substituent represented by the following general formula (2), and n represents an average degree of polymerization of the anhydroglucose and is from 50 to 5,000;

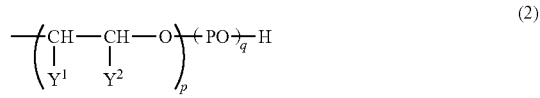

wherein, in the general formula (2), one of $Y^1$ and $Y^2$ represents a hydrogen atom and the other represents a cationic group represented by the following general formula (3), PO represents a propyleneoxy group, p represents the number of cationized ethyleneoxy groups (—CH($Y^1$)—CH($Y^2$)—O—), q represents the number of propyleneoxy groups (—PO—), and p and q each represent 0 or a positive integer, provided that a case where all p's and q's in $R^1$, $R^2$, and $R^3$ simultaneously represent 0 is excluded, and when both p and q do not represent 0, the cationized ethyleneoxy group and the propyleneoxy group may be added in any order, and when both p and q do not represent 0, and p and/or q each represent/ represents 2 or more, any one of a block bond and a random bond is permitted;

(3)

wherein, in the general formula (3), $R^4$, $R^5$, and $R^6$ each independently represent a linear or branched alkyl group having from 1 to 3 carbon atoms, and $X^-$ represents an anionic group;
(C) one or two or more organic solvents selected from the group consisting of the following components (C1) and (C2):
(C1) an aromatic alcohol represented by the following general formula (4):

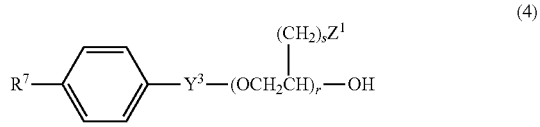

(4)

wherein, in the general formula (4), $R^7$ represents a hydrogen atom, a methyl group, or a methoxy group, $Y^3$ represents a single bond, or a linear or branched alkylene group or alkenylene group having from 1 to 3 carbon atoms, $Z^1$ represents a hydrogen atom or a hydroxyl group, and r and s each represent a number of from 0 to 5; and
(C2) a polypropylene glycol having a molecular weight of from 200 to 1,000; and
(D) one or two or more organic carboxylic acids selected from the group consisting of a hydroxy monocarboxylic acid and a dicarboxylic acid.

<2>
The aqueous hair cleansing composition according to the item <1>, in which the content of the component (A) is preferably 3% by mass or more, more preferably 5% by mass or more, even more preferably 7% by mass or more, and is preferably 20% by mass or less, more preferably 18% by mass or less, even more preferably 15% by mass or less with respect to the entirety of the aqueous hair cleansing composition.

<3>
The aqueous hair cleansing composition according to the item <1> or <2>, in which the content of the component (B) is preferably 0.01% by mass or more, more preferably 0.02% by mass or more, even more preferably 0.05% by mass or more, even more preferably 0.1% by mass or more, and is preferably 10% by mass or less, more preferably 5% by mass or less, even more preferably 2% by mass or less, even more preferably 1% by mass or less with respect to the entirety of the aqueous hair cleansing composition.

<4>
The aqueous hair cleansing composition according to any one of the items <1> to <3>, in which the mass ratio (component (B)/component (A)) of the component (B) to the component (A) is preferably 0.0005 or more, more preferably 0.001 or more, even more preferably 0.006 or more, and is preferably 0.5 or less, more preferably 0.1 or less, even more preferably 0.05 or less.

<5>
The aqueous hair cleansing composition according to any one of the items <1> to <4>, in which the content of the component (C) is preferably 0.01% by mass or more, more preferably 0.05% by mass or more, even more preferably 0.1% by mass or more, and is preferably 20% by mass or less, more preferably 10% by mass or less, even more preferably 5% by mass or less with respect to the entirety of the aqueous hair cleansing composition.

<6>
The aqueous hair cleansing composition according to any one of the items <1> to <5>, in which the mass ratio (component (B)/component (C)) of the component (B) to the component (C) is preferably 0.01 or more, more preferably 0.02 or more, even more preferably 0.04 or more, and is preferably 5 or less, more preferably 3 or less, even more preferably 1.5 or less.

<7>
The aqueous hair cleansing composition according to any one of the items <1> to <6>, in which the content of the component (D) is preferably 0.3% by mass or more, more preferably 0.5% by mass or more, even more preferably 0.7% by mass or more, and is preferably 5% by mass or less, more preferably 3% by mass or less, even more preferably 2% by mass or less with respect to the entirety of the aqueous hair cleansing composition.

<8>
The aqueous hair cleansing composition according to any one of the items <1> to <7>, in which the content of the component (A) is from 5 to 18% by mass, the content of the component (B) is from 0.02 to 5% by mass, the content of the component (C) is from 0.05 to 10% by mass, and the content of the component (D) is from 0.5 to 3% by mass.

<9>
The aqueous hair cleansing composition according to any one of the items <1> to <8>, in which the component (A) is one or more kinds represented by the following general formula (11):

$$R^{11}O(OH_2CH_2O)_uSO_3M \quad (11)$$

wherein, in the general formula (11), $R^{11}$ represents an alkyl group or alkenyl group having from 10 to 18 carbon atoms, M represents an alkali metal, an alkaline earth metal, ammonium, an alkanolamine, or a basic amino acid, and u represents the average number of added moles of ethylene oxide and represents a number of from 0.5 to 5 in terms of a mass average.

<10>
The aqueous hair cleansing composition according to any one of the items <1> to <9>, in which the component (C) in the aqueous hair cleansing composition is one or more kinds selected from the group consisting of benzyl alcohol, 2-benzyloxy ethanol, and a polypropylene glycol having a molecular weight of from 200 to 700.

<11>
The aqueous hair cleansing composition according to any one of the items <1> to <10>, in which the component (D) is one or more kinds selected from the group consisting of lactic acid, glycolic acid, malic acid, and tartaric acid.

<12>
The aqueous hair cleansing composition according to any one of the items <1> to <11>, in which with regard to each of $R^1$, $R^2$, and $R^3$ in the general formula (1), p and q in the general formula (2) each represent 0 or 1.

<13>

The aqueous hair cleansing composition according to any one of the items <1> to <12>, in which with regard to each of $Y^1$ and $Y^2$ in the general formula (2), $R^4$, $R^5$, and $R^6$ in the general formula (3) each independently represent a methyl group or an ethyl group.

<14>

The aqueous hair cleansing composition according to any one of the items <1> to <13>, in which the component (B) is a cationized hydroxypropyl cellulose obtained by a production method including the following first step and second step:

first step: a step involving adding a cationizing agent to pulp, performing a crystallinity reduction through a pulverizer treatment, adding a base to the resultant, and performing a reaction between the pulp and the cationizing agent, while performing a crystallinity reduction through a pulverizer treatment, to provide a cationized cellulose; and second step: a step involving causing the cationized cellulose obtained in the first step and propylene oxide to react with each other to provide the cationized hydroxypropyl cellulose.

EXAMPLES

The term "%" in the following examples and comparative examples means "% by mass" unless otherwise stated. In addition, methods of measuring various physical properties are as described below.

(1) Measurement of Water Contents of Pulp and Powdery Cellulose

The water contents of pulp and a powdery cellulose were measured with an infrared moisture meter (manufactured by Kett Electric Laboratory, "FD-610"). The measurement was terminated at the point of time at which a mass change ratio as measured at 120° C. for 30 seconds was 0.1% or less.

(2) Calculation of Degrees of Crystallinity of Pulp and Powdery Cellulose

The degrees of crystallinity were each calculated from the peak intensity of a diffraction spectrum measured with a "Rigaku RINT 2500VCX-RAY diffractometer" manufactured by Rigaku Corporation under the following conditions on the basis of the equation (31).

X-ray source: Cu/Kα-radiation, tube voltage: 40 kV, tube current: 120 mA

Measurement range: 2θ=5 to 45°

Measurement sample: a sample produced by compressing a pellet having an area of 320 mm² and a thickness of 1 mm Scan speed of X-ray: 10°/min When the resultant degrees of crystallinity was a negative values, all the degrees of crystallinity were defined as 0%.

(3) Calculation of Degrees of Substitution of C-HPC with Cationized Ethyleneoxy Groups and Propyleneoxy Groups The C-HPC obtained in a production example to be described later was purified by passing through a dialysis membrane (a molecular weight cut off of 1,000). After that, the aqueous solution was freeze-dried to obtain a purified C-HPC. The content (%) of chlorine in the resultant purified C-HPC was measured by elemental analysis, and then the amount (a (mol/g)) of a cationized ethyleneoxy group (—CH($Y^1$)—CH($Y^2$)—O—) in the unit mass of the C-HPC was determined from the following equation (32) after the number of cationic groups in the C-HPC and the number of chloride ions as counter ions had been approximated to be equal to each other.

$a$ (mol/g)=chlorine content (%) determined from elemental analysis/(35.5×100) (32)

In addition, a hydroxypropoxy group content (%) was measured in accordance with the "method of analyzing hydroxypropyl cellulose" described in the Japanese Pharmacopoeia except that an analysis object was not a hydroxypropyl cellulose but the purified C-HPC. The amount (b (mol/g)) of a hydroxypropoxy group (having a formula weight ($OC_3H_6OH$) of 75.09) in the unit mass of the C-HPC was determined from the following equation (33).

$b$ (mol/g)=hydroxypropoxy group content (%) determined from gas chromatographic analysis/(75.09×100) (33)

The degree of substitution (k) with cationized ethyleneoxy groups and the degree of substitution (m) with propyleneoxy groups were calculated by applying the a and b thus obtained to the following equations (34) and (35).

$a=k/(162+k \times K+m \times 58)$ (34)

$b=m/(162+k \times K+m \times 58)$ (35)

In the equations (34) and (35), k represents the degree of substitution with cationized ethyleneoxy groups, K represents the formula weight of the cationized ethyleneoxy group, and m represents the degree of substitution with propyleneoxy groups.

(4) Measurement of Average Degree of Polymerization (Copper-Ammonia Method)

(4-1) Measurement of Viscosity Average Degrees of Polymerization of Pulp and Powdery Cellulose (i) Preparation of Measurement Solution 0.5 Gram of cuprous chloride and 20 to 30 mL of 25% ammonia water were added to a measuring flask (100 mL), and then cuprous chloride was completely dissolved. After that, 1.0 g of cupric hydroxide and 25% aqueous ammonia were added so that the amount of the mixture was slightly below the marked line. The contents in the flask was completely dissolved by stirring the mixture for 30 to 40 minutes. After that, a precisely weighed cellulose was added and then the flask was filled with the aqueous ammonia until the amount of the mixture reached the marked line. The flask was hermetically sealed so that air did not enter the flask, and then the cellulose was dissolved by stirring the mixture with a magnetic stirrer for 12 hours. Thus, a measurement solution was prepared. Measurement solutions having different concentrations were prepared by changing the amount of the cellulose to be added in the range of from 20 to 500 mg.

(ii) Measurement of Viscosity Average Degree of Polymerization

Each measurement solution (copper-ammonia solution) obtained in the section (i) was filled into an Ubbelohde viscometer, and then left at rest in a thermostat (20±0.1° C.) for 1 hour. After that, the falling speed of the solution was measured. A relative viscosity $\eta_r$ was determined from the following equation by using the falling time (t (sec)) of each of the copper-ammonia solutions having various cellulose concentrations (g/dL) and the falling time ($t_0$ (sec)) of a copper-ammonia aqueous solution to which no cellulose had been added.

$\eta_r = t/t_0$

Next, a reduced viscosity ($\eta_{sp}/c$) at each concentration was determined from the following equation.

$\eta_{sp}/c = (\eta_r - 1)/c$

In the equation, c represents the cellulose concentration (g/dL).

Further, an intrinsic viscosity [η] (dL/g) was determined by extrapolating the reduced viscosity to c=0 and then a viscosity average degree of polymerization (DP) was determined from the following equation.

$$DP = 2{,}000 \times [\eta]$$

(4-2) Measurement of Viscosity Average Degree of Polymerization of C-HPC (iii) Preparation of Measurement Solution A measurement solution was prepared in the same manner as in the "preparation of measurement solution" described in the section (i) except that a precisely weighed C-HPC was used instead of the precisely weighed cellulose.

(Iv) Measurement of Viscosity Average Degree of Polymerization

Measurement was performed in the same manner as in the "measurement of viscosity average degree of polymerization" described in the section (ii) except that a cellulose conversion concentration (g/dL) was used as the concentration of the measurement solution.

Here, the cellulose conversion concentration ($c_{cell}$) refers to the mass (g) of a cellulose skeleton portion in 1 dL of the measurement solution and is defined by the following calculation equation (36).

$$c_{cell} = u \times 162/(162 + k \times K + m \times 58) \quad (36)$$

In the equation, u represents the mass (g) of the precisely weighed C-HPC used at the time of the preparation of the measurement solution, and k, K, and m each have the same meaning as that in each of the equations (34) and (35).

Production Example 1

Production of C-HPC (1)

(1-1) Chipping Step

Sheet-shaped wood pulp (Biofloc HV10 manufactured by Tembec, average degree of polymerization: 1,508, degree of crystallinity: 74%, water content: 7.6%) was cut into chips using Sheet Pelletizer (manufactured by HORAI Co., Ltd., "SGG-220") to be turned into a 3 to 5-mm square chip shape.

(1-2) Cationization Reaction Step 1,170 Grams (amount corresponding to 0.52 mole per 1 mole of the anhydroglucose unit (hereinafter referred to as "AGU") of a cellulose) of an aqueous solution of glycidyl trimethylammonium chloride (manufactured by Sakamoto Yakuhin Kogyo Co., Ltd., water content: 20%, purity: 90% or more) (hereinafter referred to as "GMAC") were mixed with 2,100 g of the chip-shaped pulp obtained in the step (1-1) in a plastic bag. After that, the mixture was loaded into a batch-type vibrating mill ("FV-20" manufactured by CHUO KAKOHKI CO., LTD.: container total capacity: 69 L, 114 rods made of SUS304 each having a diameter of 30 mm and a length of 600 mm, and each having a circular sectional shape were used as rods, volume filling factor: 71%). A pulverization treatment (frequency: 60 Hz, amplitude: 8 mm, temperature: from 10 to 40° C.) was performed for 12 minutes to provide a powdery mixture of the cellulose and GMAC.

Further, 284 g (amount corresponding to 0.6 mole per 1 mole of the AGU) of particulate sodium hydroxide were loaded into the vibrating mill. A pulverization treatment was performed under the same conditions for 120 minutes to provide a cationized cellulose.

(1-3) Hydroxypropylation Reaction Step

170 Grams of the cationized cellulose obtained in the step (1-2) were loaded into a 1-L kneader (manufactured by IRIE SHOKAI Co., Ltd., PNV-1 Type) provided with a reflux tube and then the kneader was heated to 70° C. 51 Grams of propylene oxide (amount corresponding to 2.0 moles per 1 mole of the AGU, manufactured by KANTO CHEMICAL CO., INC., special grade reagent) were added dropwise to the kneader while the cellulose was stirred, and then a reaction was performed for 6 hours until propylene oxide was consumed and reflux stopped.

The mixture after the completion of the reaction was taken out of the kneader to provide 220 g of pale brown coarse C-HPC powder. 10.0 Grams of the coarse C-HPC powder were recovered and neutralized with lactic acid. The neutralized product was purified with a dialysis membrane (a molecular weight cut off of 1,000) for the purpose of determining its degrees of substitution with propyleneoxy groups and cationized ethyleneoxy groups, followed by the freeze-drying of the aqueous solution. Thus, a purified C-HPC (1) was obtained.

Table 1-1 shows production conditions in the foregoing steps.

In addition, the elemental analysis of the resultant purified C-HPC (1) showed that its chlorine element content was 3.80%. In addition, its hydroxypropoxy group content determined by the "method of analyzing hydroxypropyl cellulose" was 36.5%. Table 2 shows the average degree of polymerization, degree of substitution with cationized ethyleneoxy groups, and degree of substitution with propyleneoxy groups of the resultant purified C-HPC (1).

Production Example 2

Production of C-HPC (2)

(2-1) Chipping Step

Sheet-shaped wood pulp (Biofloc HV+ manufactured by Tembec, average degree of polymerization: 1,770, degree of crystallinity: 74%, water content: 7.0%) was cut into chips using Sheet Pelletizer (manufactured by HORAI Co., Ltd., "SGG-220") to be turned into a 3 to 5-mm square chip shape.

(2-2) Cationization Reaction Step 58.5 Grams (amount corresponding to 0.2 mole per 1 mole of AGU) of GMAC were mixed with 100 g of the chip-shaped pulp obtained in the step (2-1) in a mortar. After that, the mixture was loaded into a batch-type vibrating mill ("MB-1" manufactured by CHUO KAKOHKI CO., LTD.: container total capacity: 3.5 L, 13 rods made of SUS304 each having a diameter of 30 mm and a length of 218 mm, and each having a circular sectional shape were used as rods, volume filling factor: 57%). A pulverization treatment (frequency: 20 Hz, amplitude: 8 mm, temperature: from 30 to 70° C.) was performed for 12 minutes to provide a powdery mixture of the cellulose and GMAC.

To the resultant powdery mixture added was 10.3 g (amount corresponding to 0.23 mole per 1 mole of the AGU) of a 48% aqueous solution of sodium hydroxide, and the contents were mixed in a mortar. After that, the mixture was loaded into the batch-type vibrating mill. A pulverization treatment was performed under the same conditions for 60 minutes to provide cationized cellulose.

(2-3) Hydroxypropylation Reaction Step

127 Grams of the cationized cellulose obtained in the step (2-2) were loaded into the 1-L kneader provided with a reflux tube used in Production Example 1 and then the kneader was heated to 70° C. 45 Grams of propylene oxide (amount corresponding to 2.8 moles per 1 mole of the AGU) were added dropwise to the kneader while the cellulose was stirred, and then a reaction was performed for 6 hours until propylene oxide was consumed and reflux stopped to provide 181.0 g of pale brown coarse C-HPC powder.

The coarse C-HPC powder was neutralized, purified, and freeze-dried in conformity with Production Example 1 to provide a purified C-HPC (2).

Table 1-1 shows production conditions in the foregoing steps.

In addition, Table 2 shows the average degree of polymerization, degree of substitution with cationized ethyleneoxy groups, and degree of substitution with propyleneoxy groups of the resultant purified C-HPC (2).

Production Example 3

Production of C-HPC (3)

(3-1) Chipping Step

Sheet-shaped wood pulp (Biofloc HV+ manufactured by Tembec, average degree of polymerization: 1,604, α-cellulose content: 93.0%, degree of crystallinity: 74%, water content: 7.0%) was cut into chips using Sheet Pelletizer (manufactured by HORAI Co., Ltd., "SGG-220") to be turned into a 3 to 5-mm square chip shape.

The resultant chip-shaped pulp was loaded into a vacuum dryer (manufactured by Advantec Toyo Kaisha, Ltd., trade name; VO-402), and was then dried at 105° C. and 20 kPa in a stream of nitrogen for hours to provide dry chip-shaped pulp (average degree of polymerization: 1,604, α-cellulose content: 99.2%, degree of crystallinity: 74%, water content: 0.80).

(3-2) Production of Alkali Cellulose (Step 1)

920 Grams of the resultant dry chip-shaped pulp were loaded into a vibrating rod mill (manufactured by CHUO KAKOHKI CO., LTD., trade name; "FV-10," total container amount; 35 L, rod diameter; 30 mm, number of rods used; 63, rod length; 510 mm, each rod had a circular sectional shape and was made of SUS304, volume filling factor; 70%), and then a pulverizer treatment was performed at an amplitude of 8 mm, 20 Hz, and from 10 to 40° C. for 10 minutes to provide 920 g of powdery pulp whose degree of crystallinity had been reduced (average degree of polymerization: 1,198, degree of crystallinity: 14%, water content: 1.0%) as a cellulose-containing raw material.

(Step 2)

530 Grams of the powdery pulp obtained as the cellulose-containing raw material in the step 1 were loaded into a mixing machine (manufactured by MATSUBO Corporation, "Loedige Mixer," capacity: 5 L), and then 307 g (amount corresponding to 1.0 mole per 1 mole of the AGU of the cellulose in the cellulose-containing raw material (hereinafter sometimes referred to as "raw material cellulose") and 33.3% of water with respect to the raw material cellulose) of a 43% aqueous solution of NaOH were added by spraying for 20 seconds while the pulp was stirred at numbers of revolutions of a main blade and a chopper blade of 250 rpm and 2,500 rpm, respectively. After the spraying, the temperature in the mixing machine was increased to 50° C., and then stirring and aging were performed for 2.5 hours to provide an alkali cellulose mixture.

(3-3) Etherification Reaction Step; Hydroxypropylation Reaction Step

While 720.4 g of the alkali cellulose mixture obtained in the step 2 were stirred in the Loedige Mixer at numbers of revolutions of the main blade and the chopper blade of 50 rpm and 400 rpm, respectively, the mixer was heated to 50° C. After that, 571.4 g (amount corresponding to 3.5 moles per 1 mole of the AGU of the alkali cellulose mixture) of propylene oxide were added dropwise for 3.5 hours. After the completion of the dropping, aging was performed at 50° C. for 2 hours.

(3-4) Etherification Reaction Step; Cationization Reaction Step 226.4 Grams of the resultant hydroxypropyl cellulose were loaded into a high-speed mixer (manufactured by Fukae Kogyo, total capacity: 2 L). Under the stirring of the hydroxypropyl cellulose at a number of revolutions of a main blade of 337 rpm (peripheral speed: 3 m/s) and a number of revolutions of a sub-blade of 1,800 rpm, a 500-mL metal container was placed in the upper portion of the mixer through a ball valve and then 109.1 g of 3-chloro-2-hydroxypropyl trimethylammonium chloride (manufactured by Yokkaichi Chemical Co., Ltd., water content: 30%, purity: 70%) were loaded into the container. The jacket was heated, temperature control (inner temperature: 50° C.) was performed, and stirring was performed for 2 hours. Thus, a coarse C-HPC was obtained.

The coarse C-HPC was neutralized with lactic acid. The neutralized product was purified with a dialysis membrane (a molecular weight cut off of 1,000) for the purpose of determining its degree of substitution with propyleneoxy groups, followed by the freeze-drying of the aqueous solution. Thus, a purified C-HPC (3) was obtained.

Table 1-2 shows production conditions in the foregoing steps.

In addition, as a result of its analysis, the C-HPC (3) had a degree of substitution with propyleneoxy groups of 1.7, a degree of substitution with cationic groups of 0.3, and an average degree of polymerization of 696 as shown in Table 2.

Production Example 4

Production of C-HPC (4)

(4-1) Chipping Step

Sheet-shaped wood pulp (Biofloc HV+ manufactured by Tembec, average degree of polymerization: 1,604, α-cellulose content: 93.0%, degree of crystallinity: 74%, water content: 7.0%) was cut into chips using Sheet Pelletizer (manufactured by HORAI Co., Ltd., "SGG-220") to be turned into a 3 to 5-mm square chip shape.

The resultant chip-shaped pulp was loaded into a vacuum dryer (manufactured by Advantec Toyo Kaisha, Ltd., trade name; VO-402), and was then dried at 105° C. and 20 kPa in a stream of nitrogen for hours to provide dry chip-shaped pulp (average degree of polymerization: 1,604, α-cellulose content: 99.2%, degree of crystallinity: 74%, water content: 0.8%).

(4-2) Production of Alkali Cellulose (Step 1)

920 Grams of the resultant dry chip-shaped pulp were loaded into a vibrating rod mill (manufactured by CHUO KAKOHKI CO., LTD., trade name; "FV-10," total container amount; 35 L, rod diameter; 30 mm, number of rods used; 63, rod length; 510 mm, each rod had a circular sectional shape and was made of SUS304, volume filling factor; 70%), and then a pulverizer treatment was performed at an amplitude of 8 mm, 20 Hz, and from 10 to 40° C. for 10 minutes to provide 920 g of powdery pulp whose degree of crystallinity had been reduced (average degree of polymerization: 1,198, degree of crystallinity: 14%, water content: 1.0%) as a cellulose-containing raw material.

(Step 2)

4,450 Grams of the powdery pulp obtained as the cellulose-containing raw material in the step (1) were loaded into a mixing machine (manufactured by Pacific Machinery & Engineering Co., Ltd., "Ploughshare Mixer," capacity: 75 L), and then 2,580 g (amount corresponding to 1.0 mole per 1 mole of the AGU of the raw material cellulose and 31% of water with respect to the raw material cellulose) of a 43% aqueous solution of NaOH were added by spraying for 1.5 minutes while the pulp was stirred at a peripheral speed of a main blade and a number of revolutions of a chopper blade of 3 m/s and 1,800 rpm, respectively. After the spraying, the mixing machine was heated to 50° C., and then stirring and aging were performed for 3 hours to provide an alkali cellulose mixture.

(4-3) Etherification Reaction Step; Hydroxypropylation Reaction Step

While 7,030 g of the alkali cellulose mixture obtained in the step 2 were stirred in the Ploughshare Mixer at a peripheral speed of the main blade and a number of revolutions of the chopper blade of 1 m/s and 400 rpm, respectively, the temperature in the mixer was increased to 50° C. After that, 5,580 g (amount corresponding to 3.5 moles per 1 mole of the AGU of the alkali cellulose mixture) of propylene oxide were dropped for 6 hours. After the completion of the dropping, aging was performed at 50° C. for 3 hours.

(4-4) Etherification Reaction Step; Cationization Reaction Step 192.0 Grams of the resultant hydroxypropyl cellulose were loaded into a high-speed mixer (manufactured by Fukae Kogyo, total capacity: 2 L). Under the stirring of the hydroxypropyl cellulose at a number of revolutions of a main blade of 337 rpm (peripheral speed: 3 m/s) and a number of revolutions of a sub-blade of 1,800 rpm, a 500-mL metal container was placed in the upper portion of the mixer through a ball valve and then 95.08 g of 3-chloro-2-hydroxypropyl trimethylammonium chloride (manufactured by Yokkaichi Chemical Co., Ltd., water content: 30%, purity: 70%) were loaded into the container. The jacket was heated, temperature control (inner temperature: 50° C.) was performed, and stirring was performed for 2 hours. Thus, a coarse C-HPC was obtained.

The coarse C-HPC was neutralized with lactic acid. The neutralized product was purified with a dialysis membrane (a molecular weight cut off of 1,000) for the purpose of determining its degree of substitution with propyleneoxy groups, followed by the freeze-drying of the aqueous solution. Thus, a purified C-HPC (4) was obtained.

Table 1-2 shows production conditions in the foregoing steps.

In addition, as a result of its analysis, the C-HPC had a degree of substitution with propyleneoxy groups of 2.0, a degree of substitution with cationic groups of 0.3, and an average degree of polymerization of 588 as shown in Table 2.

TABLE 1-1

| | Raw material pulp | | | Cationization step | | | | | |
|---|---|---|---|---|---|---|---|---|---|
| | Degree of crystallinity (%) | Average degree of polymerization | Water content (%) | Amount of pulp used (g) | Vibrating mill | Addition amount of GMAC (g) | Pulverization time (minute(s)) | Addition amount of 48% NaOH (g) | Pulverization time (minute(s)) |
| Production Example 1 C-HPC (1) | 74 | 1,508 | 7.6 | 2,100 | FV-20 | 1,170 | 12 | 284 | 120 |
| Production Example 2 C-HPC (2) | 74 | 1,770 | 7.0 | 100 | MB-1 | 58.5 | 12 | 10.3 | 60 |

| | Hydroxypropylation step | | | C-HPC | | |
|---|---|---|---|---|---|---|
| | Usage of cationized cellulose (g) | Addition amount of propylene oxide g) | Reaction time (hr) | Average degree of polymerization | Chlorine content (%) | Hydroxypropoxy group content (g) |
| Production Example 1 C-HPC (1) | 170 | 51 | 6 | 1,302 | 3.80 | 36.5 |
| Production Example 2 C-HPC (2) | 127 | 45 | 6 | 170 | 4.01 | 28.3 |

TABLE 1-2

| | Raw material pulp | | | Pulverization step | | | Hydroxypropylation step | | | |
|---|---|---|---|---|---|---|---|---|---|---|
| | Degree of crystallinity (%) | Average degree of polymerization | Water content (%) | Amount of chip-shaped pulp used (g) | mill | Pulverization time (minute(s)) | Amount of powdery pulp used (g) | Addition amount of 43% NaOH (g) | Addition amount of propylene oxide (g) | Reaction time (hr) |
| Production Example 3 C-HPC (3) | 74 | 1,604 | 7.0 | 920 | FV-10 | 10 | 530 | 307 | 571.4 | 7 |

TABLE 1-2-continued

| Production Example 4 C-HPC (4) | 74 | 1,604 | 7.0 | 920 | FV-10 | 10 | 4,450 | 2,580 | 5,580 | 9 |

| | Cationization step | | | C-HPC | | |
|---|---|---|---|---|---|---|
| | Amount of HPC used (g) | Addition amount of HAC (g) | Reaction time (hr) | Average degree of polymerization | Chlorine content (%) | Hydroxypropoxy group content (g) |
| Production Example 3 C-HPC (3) | 226 | 109 | 2 | 696 | 2.98 | 32.8 |
| Production Example 4 C-HPC (4) | 192 | 95 | 2 | 588 | 3.71 | 35.6 |

TABLE 2

| | | Average degree of polymerization | Degree of substitution with cationized ethyleneoxy groups | Degree of substitution with propyleneoxy groups |
|---|---|---|---|---|
| Production Example 1 | C-HPC (1) | 1,302 | 0.3 | 1.3 |
| Production Example 2 | C-HPC (2) | 170 | 0.3 | 1.0 |
| Production Example 3 | C-HPC (3) | 696 | 0.3 | 1.7 |
| Production Example 4 | C-HPC (4) | 588 | 0.3 | 2.0 |

Examples 1 to 7 and Comparative Examples 1 to 5

Aqueous hair cleansing compositions were prepared according to formulations shown in Table 3 and evaluated by methods to be described later. Table 3 shows the results of the evaluations as well. It should be noted that the pH is a value at 25° C. when a composition is diluted 20-fold by mass with water. In addition, in Table 3, a numerical value showing a formulation is represented in a % by mass unit.

(Methods of Evaluating Aqueous Hair Cleansing Composition)

The hair of a Japanese woman subjected to one straight perm treatment and two bleaching treatments were defined as damaged hair, and five panelists each performed the sensory evaluations of 10 g of a bundle of such hair while treating the bundle according to the following methods.

(1) Absence of Entanglement of Hair after Drying

The bundle of damaged hair (having a length of 25 cm, a width of 5.5 cm, and a weight of 10 g) was lightly rinsed with hot water having a temperature of 40° C. After that, redundant moisture was removed and then the bundle was sufficiently foamed with 0.5 g of an aqueous hair cleansing composition for about 30 seconds. After that, the hair bundle with foam was rinsed with hot water having a temperature of 40° C. at a flow rate of 2 L/min. The hair bundle was dried with a dryer and then a sensory evaluation for the difficulty with which the hair was entangled after sufficient drying was performed by the following five criteria. The evaluation was performed by five persons and their integrated value was determined.
5: Hardly entangled
4: Not entangled to a large extent
3: Felt to be normal
2: Entangled to some extent
1: Entangled (2) Luster of Hair after Drying The bundle of damaged hair (having a length of 25 cm, a width of 5.5 cm, and a weight of 10 g) was lightly rinsed with hot water having a temperature of 40° C. After that, redundant moisture was removed and then the bundle was sufficiently foamed with 0.5 g of an aqueous hair cleansing composition for about 30 seconds. After that, the hair bundle with foam was rinsed with hot water having a temperature of 40° C. at a flow rate of 2 L/min. After that, the hair bundle was dried with a dryer and then a sensory evaluation for the luster of the hair after sufficient drying was performed by the following five criteria. The evaluation was performed by five persons and their integrated value was determined.
5: Very lustrous
4: Lustrous
3: Somewhat lustrous
2: Not very lustrous
1: Not lustrous (3) Absence of Volume of Hair after Drying The bundle of damaged hair (having a length of 25 cm, a width of 5.5 cm, and a weight of 10 g) was lightly rinsed with hot water having a temperature of 40° C. After that, redundant moisture was removed and then the bundle was sufficiently foamed with 0.5 g of an aqueous hair cleansing composition for about 30 seconds. After that, the hair bundle with foam was rinsed with hot water having a temperature of 40° C. at a flow rate of 2 L/min. After that, the hair bundle was dried with a dryer and then a sensory evaluation for the difficulty with which the hair volume was expanded after sufficient drying was performed by the following five criteria. The evaluation was performed by five persons and their integrated value was determined.
5: Volumeless hair
4: Hair volume is not expanded to a very large extent.
3: Hair volume is not expanded.
2: Hair volume is expanded to some extent.
1: Hair volume is expanded.

(4) Bounce and Resilience of Hair after Drying

The bundle of damaged hair (having a length of 25 cm, a width of 5.5 cm, and a weight of 10 g) was lightly rinsed with hot water having a temperature of 40° C. After that, redundant moisture was removed and then the bundle was sufficiently foamed with 0.5 g of an aqueous hair cleansing composition for about 30 seconds. After that, the hair bundle with foam was rinsed with hot water having a temperature of 40° C. at a flow rate of 2 L/min. After that, the hair bundle was dried with a dryer and then a sensory evaluation for the bounce and resilience of hair after sufficient drying was performed by the following five criteria. The evaluation was performed by five persons and their integrated value was determined.
5: Hair has extremely high degrees of bounce and resilience.
4: Hair has bounce and resilience.
3: Hair has some degrees of bounce and resilience.
2: Hair does not have a very high degree of bounce or resilience.
1: Hair does not have bounce or resilience.
(5) Smoothness of Surface of Hair after Drying The bundle of damaged hair (having a length of 25 cm, a width of 5.5 cm, and a weight of 10 g) was lightly rinsed with hot water having a temperature of 40° C. After that, redundant moisture was removed and then the bundle was sufficiently foamed with 0.5 g of an aqueous hair cleansing composition for about 30 seconds. After that, the hair bundle with foam was rinsed with hot water having a temperature of 40° C. at a flow rate of 2 L/min. After that, the hair bundle was dried with a dryer and then a sensory evaluation for the smoothness of the surface of hair after sufficient drying was performed by the following five criteria. The evaluation was performed by five persons and their integrated value was determined.
5: Surface of hair is extremely smooth.
4: Surface of hair is smooth.
3: Surface of hair is somewhat smooth.
2: Surface of hair is not very smooth.
1: Surface of hair is not smooth.

TABLE 3

| | | Example | | | | | | |
|---|---|---|---|---|---|---|---|---|
| | | 1 | 2 | 3 | 4 | 5 | 6 | 7 |
| (A) | Ammonium lauryl ether (1) sulfate*[1] | 12.5 | — | 12.5 | 12.5 | 12.5 | 12.5 | 12.5 |
| | Sodium lauryl ether (2) sulfate*[2] | — | 12.5 | — | — | — | — | — |
| (B) | C-HPC (1)*[3] | 0.3 | 0.3 | — | 0.1 | 0.5 | 0.3 | 0.3 |
| | C-HPC (2)*[4] | — | — | 0.3 | — | — | — | — |
| (C) | Benzyl alcohol | 0.3 | 0.3 | 0.3 | 0.3 | 0.3 | 0.1 | 3 |
| | Polypropylene (7) glycol*[5] | 0.05 | 0.05 | 0.05 | 0.05 | 0.05 | 0.01 | 0.5 |
| (D) | Malic acid | 0.55 | 0.55 | 0.55 | 0.55 | 0.55 | 0.55 | 0.55 |
| | Lactic acid | 0.2 | 0.2 | 0.2 | 0.2 | 0.2 | 0.2 | 0.2 |
| | Hydroxypropyl cellulose (HPC)*[6] | — | — | — | — | — | — | — |
| | Cationized hydroxyethyl cellulose (C-HEC)*[7] | — | — | — | — | — | — | — |
| | Lauryl hydroxy sulfobetaine*[11] | 1.7 | 1.7 | 1.7 | 1.7 | 1.7 | 1.7 | 1.7 |
| | Lauric acid | 0.4 | 0.4 | 0.4 | 0.4 | 0.4 | 0.4 | 0.4 |
| | Isodecyl glyceryl ether | 1.64 | 1.64 | 1.64 | 1.64 | 1.64 | 1.64 | 1.64 |
| | Polyoxyethylene (6) stearyl ether*[8] | 2.6 | 2.6 | 2.6 | 2.6 | 2.6 | 2.6 | 2.6 |
| | Ethylene glycol distearyl | 1.6 | 1.6 | 1.6 | 1.6 | 1.6 | 1.6 | 1.6 |
| | Cationized guar gum*[9] | 0.2 | 0.2 | 0.2 | 0.2 | 0.2 | 0.2 | 0.2 |
| | Dimethylpolysiloxane emulsion*[10] | 0.3 | 0.3 | 0.3 | 0.3 | 0.3 | 0.3 | 0.3 |
| | Sodium benzoate | 0.1 | 0.1 | 0.1 | 0.1 | 0.1 | 0.1 | 0.1 |
| | Sodium chloride | 0.4 | 0.4 | 0.4 | 0.4 | 0.4 | 0.4 | 0.4 |
| | Sodium hydroxide | *12 | *12 | *12 | *12 | *12 | *12 | *12 |
| | Purified water | Balance | Balance | Balance | Balance | Balance | Balance | Balance |
| | Total | 100 | 100 | 100 | 100 | 100 | 100 | 100 |
| | (B)/(A) | 0.024 | 0.024 | 0.024 | 0.008 | 0.04 | 0.024 | 0.024 |
| | (B)/(C) | 0.86 | 0.86 | 0.86 | 0.29 | 1.43 | 2.73 | 0.09 |
| | pH | 3.7 | 3.7 | 3.7 | 3.7 | 3.7 | 3.7 | 3.7 |
| | Absence of entanglement of hair after drying | 22 | 21 | 22 | 20 | 22 | 21 | 22 |
| | Luster of hair after drying | 23 | 22 | 22 | 21 | 23 | 22 | 23 |
| | Absence of volume of hair after drying | 23 | 24 | 22 | 21 | 23 | 22 | 22 |
| | Bounce and resilience of hair after drying | 23 | 23 | 23 | 22 | 23 | 23 | 24 |
| | Smoothness of surface of hair after drying | 24 | 23 | 24 | 21 | 24 | 23 | 23 |

| | | Comparative Example | | | | |
|---|---|---|---|---|---|---|
| | | 1 | 2 | 3 | 4 | 5 |
| (A) | Ammonium lauryl ether (1) sulfate*[1] | 12.5 | 12.5 | 12.5 | 12.5 | 12.5 |
| | Sodium lauryl ether (2) sulfate*[2] | — | — | — | — | — |
| (B) | C-HPC (1)*[3] | — | — | — | 0.3 | 0.3 |
| | C-HPC (2)*[4] | — | — | — | — | — |
| (C) | Benzyl alcohol | 0.3 | 0.3 | 0.3 | 0.3 | — |
| | Polypropylene (7) glycol*[5] | 0.05 | 0.05 | 0.05 | 0.05 | — |
| (D) | Malic acid | 0.55 | 0.55 | 0.55 | 0.1 | 0.55 |
| | Lactic acid | 0.2 | 0.2 | 0.2 | 0.18 | 0.2 |
| | Hydroxypropyl cellulose (HPC)*[6] | 0.3 | — | — | — | — |
| | Cationized hydroxyethyl cellulose (C-HEC)*[7] | — | 0.3 | — | — | — |
| | Lauryl hydroxy sulfobetaine*[11] | 1.7 | 1.7 | 1.7 | 1.7 | 1.7 |
| | Lauric acid | 0.4 | 0.4 | 0.4 | 0.4 | 0.4 |
| | Isodecyl glyceryl ether | 1.64 | 1.64 | 1.64 | 1.64 | 1.64 |
| | Polyoxyethylene (6) stearyl ether*[8] | 2.6 | 2.6 | 2.6 | 2.6 | 2.6 |
| | Ethylene glycol distearyl | 1.6 | 1.6 | 1.6 | 1.6 | 1.6 |
| | Cationized guar gum*[9] | 0.2 | 0.2 | 0.2 | 0.2 | 0.2 |
| | Dimethylpolysiloxane emulsion*[10] | 0.3 | 0.3 | 0.3 | 0.3 | 0.3 |
| | Sodium benzoate | 0.1 | 0.1 | 0.1 | 0.1 | 0.1 |

TABLE 3-continued

|  |  |  |  |  |  |
|---|---|---|---|---|---|
| Sodium chloride | 0.4 | 0.4 | 0.4 | 0.4 | 0.4 |
| Sodium hydroxide | *12 | *12 | *12 | *12 | *12 |
| Purified water | Balance | Balance | Balance | Balance | Balance |
| Total | 100 | 100 | 100 | 100 | 100 |
| (B)/(A) | 0 | 0 | 0 | 0.024 | 0.024 |
| (B)/(C) | 0 | 0 | 0 | 0.86 | — |
| pH | 3.7 | 3.7 | 3.7 | 6 | 3.7 |
| Absence of entanglement of hair after drying | 15 | 16 | 9 | 17 | 15 |
| Luster of hair after drying | 16 | 18 | 13 | 14 | 13 |
| Absence of volume of hair after drying | 15 | 17 | 12 | 15 | 15 |
| Bounce and resilience of hair after drying | 19 | 18 | 18 | 15 | 19 |
| Smoothness of surface of hair after drying | 13 | 12 | 11 | 19 | 19 |

*[1] Ammonium polyoxyethylene (1) lauryl ether sulfate: mass average number of added moles of ethylene oxide: 1
*[2] Sodium polyoxyethylene (2) lauryl ether sulfate: mass average number of added moles of ethylene oxide: 2
*[3] C-HPC (1): C-HPC represented by the general formula (1) and having a degree of substitution (k) with cationized ethyleneoxy groups of 0.3 and a degree of substitution (m) with propyleneoxy groups of 1.3 (obtained in Production Example 1)
*[4] C-HPC (2): C-HPC represented by the general formula (1) and having a degree of substitution (k) with cationized ethyleneoxy groups of 0.3 and a degree of substitution (m) with propyleneoxy groups of 1.0 (obtained in Production Example 2)
*[5] Polypropylene (7) glycol: molecular weight: 420
*[6] Raw material name: "HPC-M" (manufacturer: manufactured by NIPPON SODA CO., LTD.)
*[7] Raw material name: "POIZ C-80M" (manufacturer: manufactured by Kao Corporation)
*[8] Polyoxyethylene (6) stearyl ether: mass average number of added moles of ethylene oxide: 6
*[9] Cationized guar gum: JAGUAR C-13S (manufactured by Rhodia)
*[10] Dimethylpolysiloxane emulsion: mixture of viscosity $(10,000 \text{ mm}^2/\text{s})/(10 \text{ mm}^2/\text{s}) = 95/5$, average particle diameter: 4.0 μm, dimethylpolysiloxane: 60% by mass
*[11] Raw material name: "AMPHITOL 20HD" (manufacturer: Kao Corporation)
*12 Amount for pH adjustment Examples 8 to 11

Aqueous hair cleansing compositions were prepared according to formulations shown in Table 4 and evaluated by the same methods as those in Table 3. Table 4 shows the results of the evaluations as well. It should be noted that the pH is a value at 25° C. when a composition is diluted 20-fold by mass with water. In addition, in Table 4, a numerical value showing a formulation is represented in a % by mass unit.

TABLE 4

|  |  | Example | | | |
|---|---|---|---|---|---|
|  |  | 8 | 9 | 10 | 11 |
| (A) | Ammonium lauryl ether (1) sulfate | 12.5 | 12.5 | 12.5 | 12.5 |
| (B) | C-HPC (3)*[13] | 0.3 | — | 0.3 | 0.3 |
|  | C-HPC (4)*[14] | — | 0.3 | — | — |
| (C) | Benzyl alcohol | 0.3 | 0.3 | 0.3 | 0.3 |
|  | Polypropylene (7) glycol*[5] | 0.05 | 0.05 | 0.05 | 0.05 |
| (D) | Malic acid | 0.55 | 0.55 | 0.55 | 0.7 |
|  | Lactic acid | 0.2 | 0.2 | 0.2 | 1 |
|  | Lauryl hydroxy sulfobetaine*[11] | 1.7 | 1.7 | 1.7 | 1.7 |
|  | Lauric acid | 0.4 | 0.4 | 0.4 | 0.4 |
|  | Isodecyl glyceryl ether | 1.64 | 1.64 | 1.64 | 1.64 |
|  | Polyoxyethylene (6) stearyl ether*[8] | 2.6 | 2.6 | 2.6 | 2.6 |
|  | Ethylene glycol distearyl | 1.6 | 1.6 | 1.6 | 1.6 |
|  | Cationized guar gum*[9] | 0.2 | 0.2 | 0.2 | 0.2 |
|  | Dimethylpolysiloxane emulsion*[10] | 0.3 | 0.3 | 0.3 | 0.3 |
|  | Sodium benzoate | 0.1 | 0.1 | 0.1 | 0.1 |
|  | Sodium chloride | 0.4 | 0.4 | 0.4 | 0.4 |
|  | Sodium hydroxide | *12 | *12 | *12 | *12 |
|  | Purified water | Balance | Balance | Balance | Balance |
|  | Total | 100 | 100 | 100 | 100 |
|  | (B)/(A) | 0.024 | 0.024 | 0.024 | 0.024 |
|  | (B)/(C) | 0.86 | 0.86 | 0.86 | 0.86 |
|  | pH | 3.7 | 3.7 | 4.5 | 3.7 |
|  | Absence of entanglement of hair after drying | 22 | 22 | 22 | 22 |
|  | Luster of hair after drying | 24 | 24 | 21 | 24 |
|  | Absence of volume of hair after drying | 23 | 23 | 22 | 23 |
|  | Bounce and resilience of hair after drying | 24 | 25 | 21 | 25 |
|  | Smoothness of surface of hair after drying | 24 | 24 | 22 | 24 |

*[13] C-HPC (3): C-HPC represented by the general formula (1) and having a degree of substitution (k) with cationized ethyleneoxy groups of 0.3 and a degree of substitution (m) with propyleneoxy groups of 1.7 (obtained in Production Example 3)
*[14] C-HPC (4): C-HPC represented by the general formula (1) and having a degree of substitution (k) with cationized ethyleneoxy groups of 0.3 and a degree of substitution (m) with propyleneoxy groups of 2.0 (obtained in Production Example 4)

Examples 12 to 15

Aqueous hair cleansing compositions having the following compositions were prepared by an ordinary method and evaluated. It should be noted that the pH is a value measured at 25° C. when each composition is diluted 20-fold by mass with water.

Example 12

Shampoo (pH 3.9)

|  | (% by mass) |
|---|---|
| Ammonium lauryl ether (1) sulfate (manufactured by Kao Corporation: EMAL 125A) | 12.5 |
| C-HPC (1) (Production Example 1) | 0.3 |
| Isodecyl glyceryl ether | 1.7 |
| Polyoxyethylene (6) stearyl ether (manufactured by Kao Corporation: EMULGEN 306P) | 2.3 |
| Lauryl hydroxy sulfobetaine (manufactured by Kao Corporation: AMPHITOL 20HD) | 1.7 |
| Lauric acid (manufactured by Kao Corporation: LUNAC L-98) | 0.4 |
| Coconut oil fatty acid monoethanolamide (manufactured by Kawaken Fine Chemicals Co., Ltd.: Amisol CME) | 0.3 |

|  | (% by mass) |
|---|---|
| Malic acid | 0.75 |
| Benzyl alcohol | 0.3 |
| Ethylene glycol distearyl | 1.6 |
| Cationized guar gum (manufactured by Rhodia: JAGUAR C-14S) | 0.3 |
| Polypropylene (7) glycol (molecular weight: 420) (manufactured by ADEKA CORPORATION: ADEKA Carpol DL-30) | 0.1 |
| Dipotassium glycyrrhizate | 0.1 |
| Sodium benzoate | 0.1 |
| Ethanol | 0.3 |
| Sodium chloride | 0.4 |
| *Eucalyptus* extract | 0.1 |
| Chamomile extract | 0.05 |
| Panthenol | 0.05 |
| Silk extract | 0.05 |
| *Aloe* extract | 0.05 |
| Seaweed extract | 0.05 |
| Orange oil | 0.05 |
| Potassium hydroxide | (for adjustment to pH 3.9) |
| Perfume | q.s. |
| Purified water | Balance |

The shampoo of Example 12 is excellent in rinse-off characteristics at the time of hair washing, effectively suppresses the entanglement of hair, and the volume of hair, after drying even when hair is damaged hair, and can impart bounce and resilience to hair.

Example 13

Shampoo (pH 3.9)

|  | (% by mass) |
|---|---|
| Ammonium lauryl ether (1) sulfate (manufactured by Kao Corporation: EMAL 125A) | 12.5 |
| C-HPC (1) (Production Example 1) | 0.3 |
| Isodecyl glyceryl ether | 1.7 |
| Polyoxyethylene (6) stearyl ether (manufactured by Kao Corporation: EMULGEN 306P) | 2.3 |
| Lauryl hydroxy sulfobetaine (manufactured by Kao Corporation: AMPHITOL 20HD) | 1.0 |
| Lauramidopropyl betaine (manufactured by Kao Corporation: AMPHITOL 20AB) | 0.8 |
| Lauric acid (manufactured by Kao Corporation: LUNAC L-98) | 0.4 |
| Coconut oil fatty acid monoethanolamide (manufactured by Kawaken Fine Chemicals Co., Ltd.: Amisol CME) | 0.3 |
| Malic acid | 0.75 |
| Benzyl alcohol | 0.3 |
| Ethylene glycol distearyl | 1.6 |
| Cationized cellulose (manufactured by Kao Corporation: POIZ M-80) | 0.3 |
| Polypropylene (7) glycol (molecular weight: 420) (manufactured by ADEKA CORPORATION: ADEKA Carpol DL-30) | 0.1 |
| Dimethyldiallylammonium chloride-acrylamide copolymer solution (manufactured by The Lubrizol Corporation: Merquat 550) | 0.2 |
| Dipotassium glycyrrhizate | 0.1 |
| Dimethylpolysiloxane | 0.5 |
| Sodium benzoate | 0.1 |
| Ethanol | 0.3 |
| Sodium chloride | 0.4 |
| *Eucalyptus* extract | 0.1 |
| Chamomile extract | 0.05 |
| Panthenol | 0.05 |
| Silk extract | 0.05 |
| *Aloe* extract | 0.05 |
| Seaweed extract | 0.05 |
| Orange oil | 0.05 |
| Potassium hydroxide | (for adjustment to pH 3.9) |
| Perfume | q.s. |
| Purified water | Balance |

The shampoo of Example 13 is excellent in rinse-off characteristics at the time of hair washing, effectively suppresses the entanglement of hair, and the volume of hair, after drying even when hair is damaged hair, and can impart bounce and resilience to hair.

Example 14

Shampoo (pH 5.0)

|  | (% by mass) |
|---|---|
| Ammonium lauryl ether (1) sulfate (manufactured by Kao Corporation: EMAL 125A) | 12.5 |
| C-HPC (1) (Production Example 1) | 0.3 |
| Isodecyl glyceryl ether | 1.7 |
| Polyoxyethylene (6) stearyl ether (manufactured by Kao Corporation: EMULGEN 306P) | 2.3 |
| Lauryl hydroxy sulfobetaine (manufactured by Kao Corporation: AMPHITOL 20HD) | 1.7 |
| Lauric acid (manufactured by Kao Corporation: LUNAC L-98) | 0.4 |
| Malic acid | 0.2 |
| Benzyl alcohol | 0.3 |
| Zinc pyrithione | 1.0 |
| Ethylene glycol distearyl | 1.6 |
| Cationized cellulose (manufactured by Kao Corporation: POIZ M-80) | 0.3 |
| Polypropylene (7) glycol (molecular weight: 420) (manufactured by ADEKA CORPORATION: ADEKA Carpol DL-30) | 0.1 |
| Dipotassium glycyrrhizate | 0.1 |
| Polydimethylsiloxane | 0.5 |
| Sodium benzoate | 0.1 |
| Ethanol | 0.3 |
| Sodium chloride | 0.4 |
| Potassium hydroxide | (for adjustment to pH 5.0) |
| Perfume | q.s. |
| Purified water | Balance |

The shampoo of Example 14 is excellent in rinse-off characteristics at the time of hair washing, effectively suppresses the entanglement of hair, and the volume of hair, after drying even when hair is damaged hair, and can impart bounce and resilience to hair.

Example 15

Shampoo (pH 3.9)

|  | (% by mass) |
|---|---|
| Ammonium lauryl ether (1) sulfate (manufactured by Kao Corporation: EMAL 125A) | 12.5 |

| | (% by mass) |
|---|---|
| C-HPC (1) (Production Example 1) | 0.3 |
| Isodecyl glyceryl ether | 1.7 |
| Polyoxyethylene (6) stearyl ether (manufactured by Kao Corporation: EMULGEN 306P) | 2.3 |
| Lauryl hydroxy sulfobetaine (manufactured by Kao Corporation: AMPHITOL 20HD) | 1.7 |
| Lauric acid (manufactured by Kao Corporation: LUNAC L-98) | 0.4 |
| Malic acid | 0.75 |
| Benzyl alcohol | 0.3 |
| Ethylene glycol distearyl | 1.6 |
| Piroctone olamine (manufactured by Rhodia: Octopirox) | 0.5 |
| Cationized guar gum (manufactured by Rhodia: JAGUAR C-14S) | 0.3 |
| Polypropylene (7) glycol (molecular weight: 420) (manufactured by ADEKA CORPORATION: ADEKA Carpol DL-30) | 0.1 |
| Dipotassium glycyrrhizate | 0.1 |
| Sodium benzoate | 0.1 |
| Ethanol | 0.3 |
| Sodium chloride | 0.4 |
| Potassium hydroxide | (for adjustment to pH 3.9) |
| Perfume | q.s. |
| Purified water | Balance |

The shampoo of Example 15 is excellent in rinse-off characteristics at the time of hair washing, effectively suppresses the entanglement of hair, and the volume of hair, after drying even when hair is damaged hair, and can impart bounce and resilience to hair.

The invention claimed is:

1. An aqueous hair cleansing composition, comprising: components (A), (B), (C), and (D), and water, wherein the aqueous hair cleansing composition has a pH of from 2 to 5 at 25° C. when diluted 20-fold by mass with water:

(A) an anionic surfactant;

(B) a cationized hydroxypropyl cellulose having a main chain derived from an anhydroglucose represented by formula (1), and having a degree of substitution with cationized ethyleneoxy groups of from 0.01 to 2.9 and a degree of substitution with propyleneoxy groups of from 0.1 to 4.0:

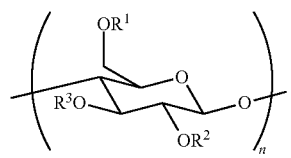

wherein, in formula (1), $R^1$, $R^2$, and $R^3$ each independently represent a substituent represented by formula (2), and n represents an average degree of polymerization of the anhydroglucose and is from 50 to 5,000;

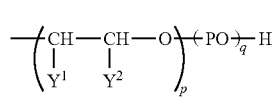

wherein, in formula (2), one of $Y^1$ and $Y^2$ represents a hydrogen atom and the other represents a cationic group represented by formula (3), PO represents a propyleneoxy group, p represents a number of cationized ethyleneoxy groups (—CH($Y^1$)—CH($Y^2$)—O—), q represents a number of propyleneoxy groups (—PO—), and p and q each represent 0 or a positive integer, provided that a case where all p's and q's in $R^1$, $R^2$, and $R^3$ simultaneously represent 0 is excluded, and when both p and q do not represent 0, the cationized ethyleneoxy group and the propyleneoxy group may be added in any order, and when both p and q do not represent 0, and p and/or q each represent/represents 2 or more, any one of a block bond and a random bond is permitted;

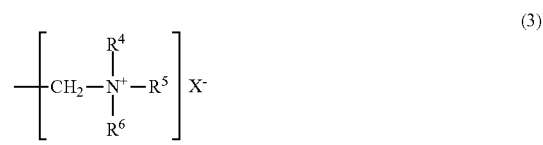

wherein, in formula (3), $R^4$, $R^5$, and $R^6$ each independently represent a linear or branched alkyl group having from 1 to 3 carbon atoms, and $X^-$ represents an anionic group;

(C) at least one organic solvent selected from the group consisting of:

(C1) an aromatic alcohol represented by formula (4):

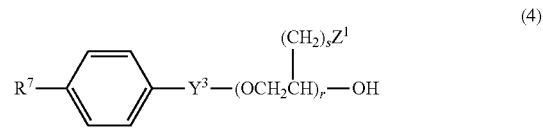

wherein, in formula (4), $R^7$ represents a hydrogen atom, a methyl group, or a methoxy group, $Y^3$ represents a single bond, or a linear or branched alkylene group or alkenylene group having from 1 to 3 carbon atoms, $Z^1$ represents a hydrogen atom or a hydroxyl group, and r and s each represent a number of 0 to 5; and (C2) a polypropylene glycol having a molecular weight of from 200 to 1,000; and (D) at least one organic carboxylic acid selected from the group consisting of a hydroxy monocarboxylic acid and a dicarboxylic acid.

2. The aqueous hair cleansing composition according to claim 1, wherein the content of component (B) is from 0.01 to 10% by mass with respect to the entirety of the aqueous hair cleansing composition.

3. The aqueous hair cleansing composition according to claim 2, wherein a mass ratio of component (B) to component (A), component (B)/component (A), is 0.0005 or more, and 0.5 or less.

4. The aqueous hair cleansing composition according to claim 1, wherein the content of component (A) is 3% by mass or more, and 20% by mass or less with respect to the entirety of the aqueous hair cleansing composition.

5. The aqueous hair cleansing composition according to claim 2, wherein a mass ratio of component (B) to component (C), component (B)/component (C), is 0.01 or more, and 5 or less.

6. The aqueous hair cleansing composition according to claim 1, wherein the content of component (C) is 0.01% by mass or more, and 20% by mass or less with respect to the entirety of the aqueous hair cleansing composition.

7. The aqueous hair cleansing composition according to claim 1, wherein the content of component (D) is 0.3% by mass or more, and 5% by mass or less with respect to the entirety of the aqueous hair cleansing composition.

8. The aqueous hair cleansing composition according to claim 1, wherein with regard to each of $R^1$, $R^2$, and $R^3$ in formula (1), p and q in formula (2) each represent 0 or 1.

9. The aqueous hair cleansing composition according to claim 1, wherein with regard to each of $Y^1$ and $Y^2$ in formula (2), $R^4$, $R^5$, and $R^6$ in formula (3) each independently represent a methyl group or an ethyl group.

10. The aqueous hair cleansing composition according to claim 1, wherein the aromatic alcohol as component (C1) is at least one member selected from the group consisting of benzyl alcohol, cinnamyl alcohol, phenethyl alcohol, p-anisyl alcohol, p-methylbenzyl alcohol, phenoxyethanol, and 2-benzyloxyethanol.

11. The aqueous hair cleansing composition according to claim 1, wherein component (C) of the aqueous hair cleansing composition is at least one member selected from the group consisting of benzyl alcohol, 2-benzyloxyethanol, and a polypropylene glycol having a molecular weight of from 200 to 700.

12. The aqueous hair cleansing composition according to claim 1, wherein component (D) is at least one member selected from the group consisting of lactic acid, glycolic acid, malic acid, and tartaric acid.

13. The aqueous hair cleansing composition according to claim 1, wherein, the content of water is 50% by mass or more, and 95% by mass or less.

14. The aqueous hair cleansing composition according to claim 1, wherein component (B) is a cationized hydroxypropyl cellulose obtained by a production method comprising:
    adding a cationizing agent to pulp, performing a crystallinity reduction through a pulverizer treatment, adding a base to the resultant, and performing a reaction between the pulp and the cationizing agent, while performing a crystallinity reduction through a pulverizer treatment, to provide a cationized cellulose; and
    reacting the cationized cellulose with propylene oxide to provide the cationized hydroxypropyl cellulose.

* * * * *